(12) United States Patent
Lee et al.

(10) Patent No.: US 7,304,146 B2
(45) Date of Patent: Dec. 4, 2007

(54) FLUOROGENIC KINASE ASSAYS AND SUBSTRATES

(75) Inventors: Linda G. Lee, Palo Alto, CA (US); Hongye Sun, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 11/035,682

(22) Filed: Jan. 14, 2005

(65) Prior Publication Data

US 2005/0245726 A1 Nov. 3, 2005

Related U.S. Application Data

(60) Provisional application No. 60/537,416, filed on Jan. 16, 2004.

(51) Int. Cl.
C07K 1/00 (2006.01)
C08H 1/00 (2006.01)
(52) U.S. Cl. .................................................. 530/402
(58) Field of Classification Search ...................... None
See application file for complete search history.

(56) References Cited

U.S. PATENT DOCUMENTS

| | | | |
|---|---|---|---|
| 5,089,392 A | 2/1992 | Miller et al. | |
| 5,210,040 A | 5/1993 | Jou et al. | |
| 5,366,895 A | 11/1994 | Rutner et al. | |
| 5,912,137 A | 6/1999 | Tsien et al. | |
| 5,925,558 A | 7/1999 | Tsien et al. | |
| 5,958,713 A | 9/1999 | Thastrup et al. | |
| 6,037,137 A | 3/2000 | Komoriya et al. | |
| 6,143,716 A | 11/2000 | Meers et al. | |
| 6,235,535 B1 | 5/2001 | Keinänen et al. | |
| 6,339,069 B1 | 1/2002 | Meers et al. | |
| 6,495,664 B1 * | 12/2002 | Cubitt | 530/350 |
| 6,498,005 B1 | 12/2002 | Nikiforov et al. | |
| 2002/0028477 A1 | 3/2002 | Goueli et al. | |
| 2002/0086336 A1 | 7/2002 | Kramer et al. | |
| 2003/0135869 A1 | 7/2003 | Farber et al. | |
| 2004/0146959 A1 | 7/2004 | Graham et al. | |
| 2005/0239217 A1 | 10/2005 | Graham et al. | |
| 2005/0244891 A1 | 11/2005 | Graham et al. | |
| 2005/0244907 A1 | 11/2005 | Graham et al. | |
| 2006/0003383 A1 | 1/2006 | Graham | |
| 2006/0035302 A1 | 2/2006 | Lee | |

FOREIGN PATENT DOCUMENTS

| | | |
|---|---|---|
| WO | WO 99/18856 | 4/1999 |
| WO | WO 99/29894 | 6/1999 |
| WO | WO 00/09539 | 2/2000 |
| WO | WO 00/18949 | 4/2000 |
| WO | WO 00/50635 | 8/2000 |
| WO | WO 00/66766 | 11/2000 |
| WO | WO 01/07638 A2 | 2/2001 |
| WO | WO 01/43778 | 6/2001 |
| WO | WO 02/079268 | 10/2002 |
| WO | WO 2004/022773 A1 | 3/2004 |
| WO | WO 05/059163 | 6/2005 |
| WO | WO 2005/054495 A2 | 6/2005 |
| WO | WO 06/002221 | 1/2006 |

OTHER PUBLICATIONS

Hendrickson H Stewart et al., "Intramolecularly quenched BODIPY-labeled phospholipids analogs in phospholipase A2 and platelet-activating factor acetylhydrolase assays and in vivo fluorescence imaging," Analytical Biochemistry, Academic Press, San Diego, CA, US, vol. 276, No. 1, Dec. 1, 1999, pp. 27-35.

Hendrickson H Stewart, "Fluorescence-based assays of lipases, phospholipases, and other lipolytic enzymes", Analytical Biochemistry, Academic Press, New York, NY, US, vol. 219, No. 1, 1994, pp. 1-8.

Lee Jong-Hoon et al., "Polymeric nanoparticle composed of fatty acids and poly(ethylene glycol) as a drug carrier." International Journal of Pharmaceutics, Jan. 30, 2003, vol. 251, No. 1-2; Jan. 30, 2003, pp. 23-32.

International Search Report for International Application No. PCT/US2005/001784.

Lee, et. al., 2002, Abstract, IBC Conference, Sep. 9-10, Boston.
Matveeva, et al., 1996, Anal. Biochem., 234:13-18.
Noble, et al., 2003, Anal. Chem., 75(9):2042-2047.
Shults and Imperiali, 2003, JACS, 125:14248-14249.
Sun, et al., 2003, Abstract, SBS Conference, p. 217.
Sun, et al., 2005, Anal. Chem., 77(7):2043-2049.
Yamaji, et al., 1997, J. Fermentation & Bioengineering, 83(6):596-598.
Chen, et al., 2002, JACS, 124:3840-3841.
Tan, et al., 2002, JACS, 124:11827-11832.
Promega Technical Bulletin No. 132.
Byk, et al., 1998, J. Med. Chem., 41:224-235.
Pap, et al., 1995, J. Bio. Chem., 270(3):1254-1260.
Yeh, et al., 2002, J. Bio. Chem., 277(13):11527-11532.
Jeong and Nikiforov, 1999, BiTechniques 27:1232-1238.
Sharma et al., 2007, "Deep Quench: An Expanded Dynamic Range for Protein Kinase Sensors," *J. American Chemical Society*, 129:2742-2743.
Sun et al., 2005, "Real-Time Protein Kinases Assay," *Anal. Chem.*, 77:2043-2049.
Veldhuyzen et al., 2003, "A Light-Activiated Proble of Intracellular Protein Kinase Activity," *J. American Chemical Society*, 125:13358-13359.
Yeh et al., 2002, "Real Time Visualization of Protein Kinase Activity in Living Cells," *The Journal of Biological Chemistry*, 277(13):11527-11532.

\* cited by examiner

*Primary Examiner*—Ralph Gitomer
*Assistant Examiner*—Bin Shen
(74) *Attorney, Agent, or Firm*—Dechert LLP

(57) ABSTRACT

Disclosed are fluorescent compositions and methods for detecting and/or characterizing enzymes and various uses thereof.

31 Claims, 9 Drawing Sheets

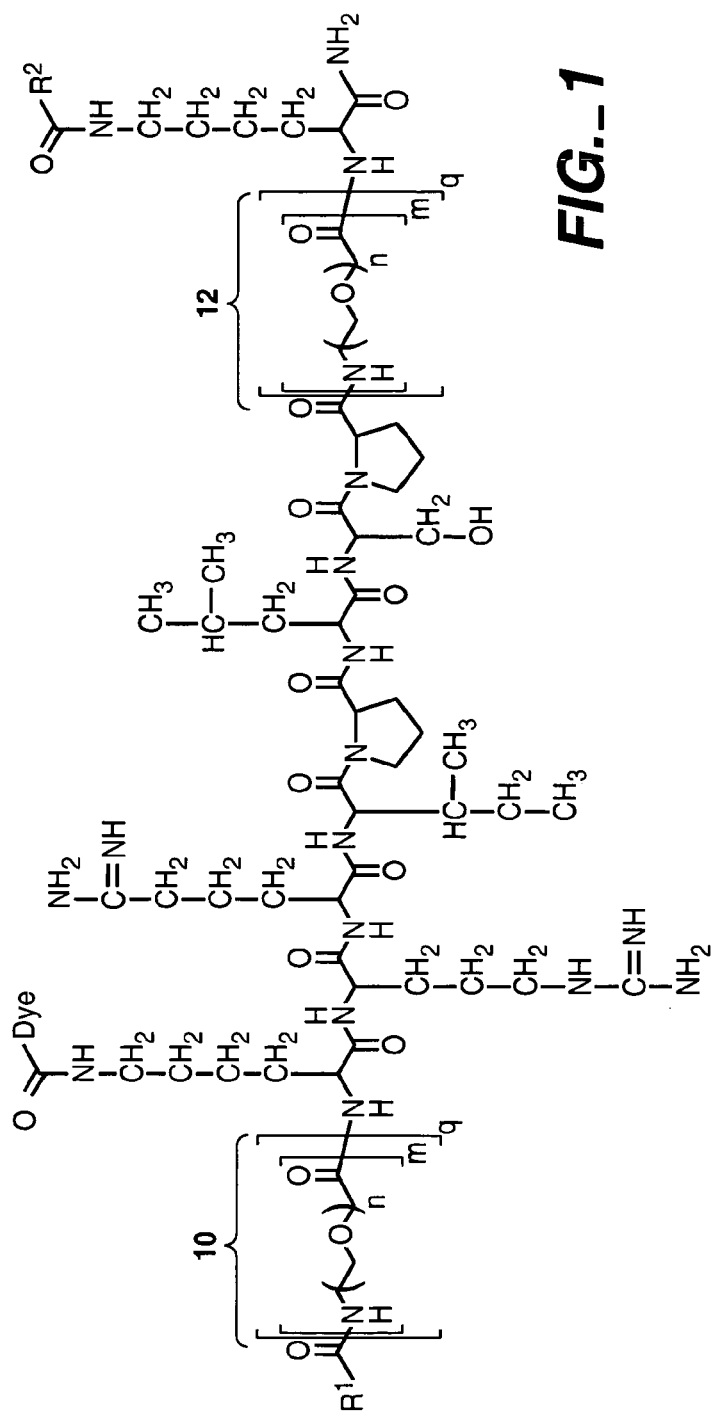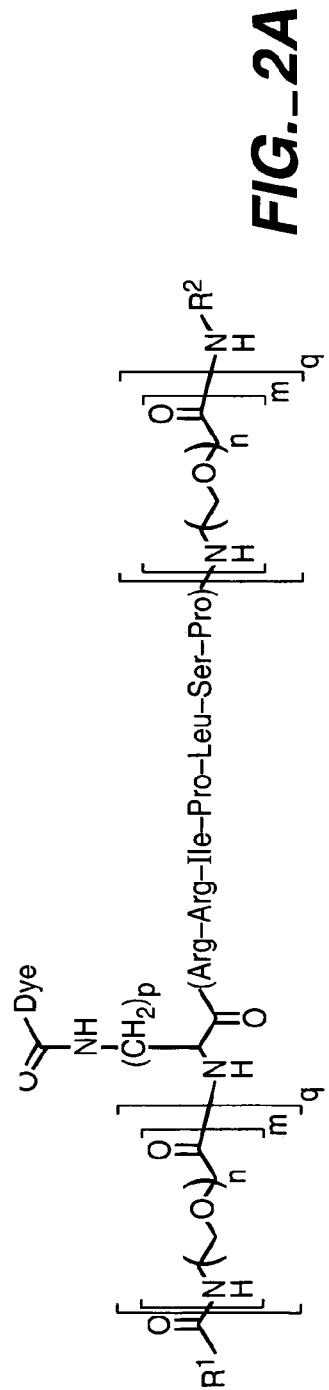
FIG._1
FIG._2A

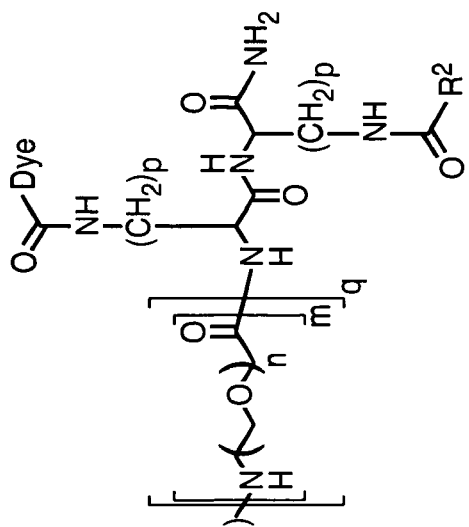
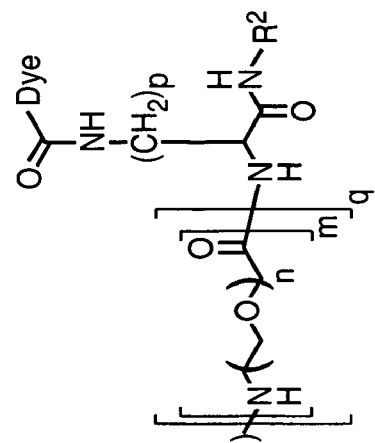
FIG._2B
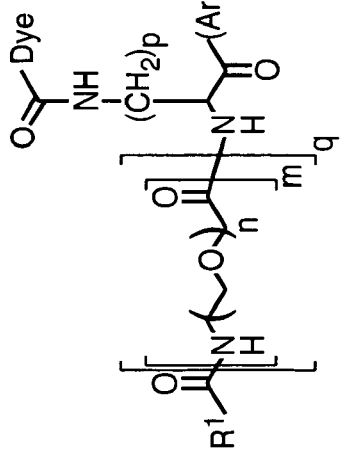
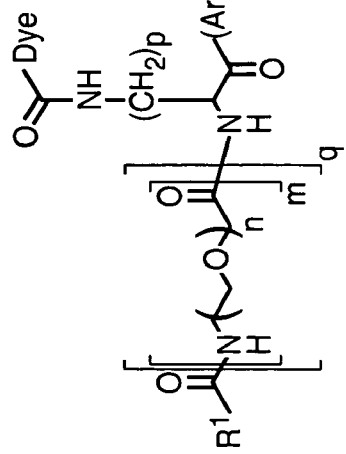
FIG._2C

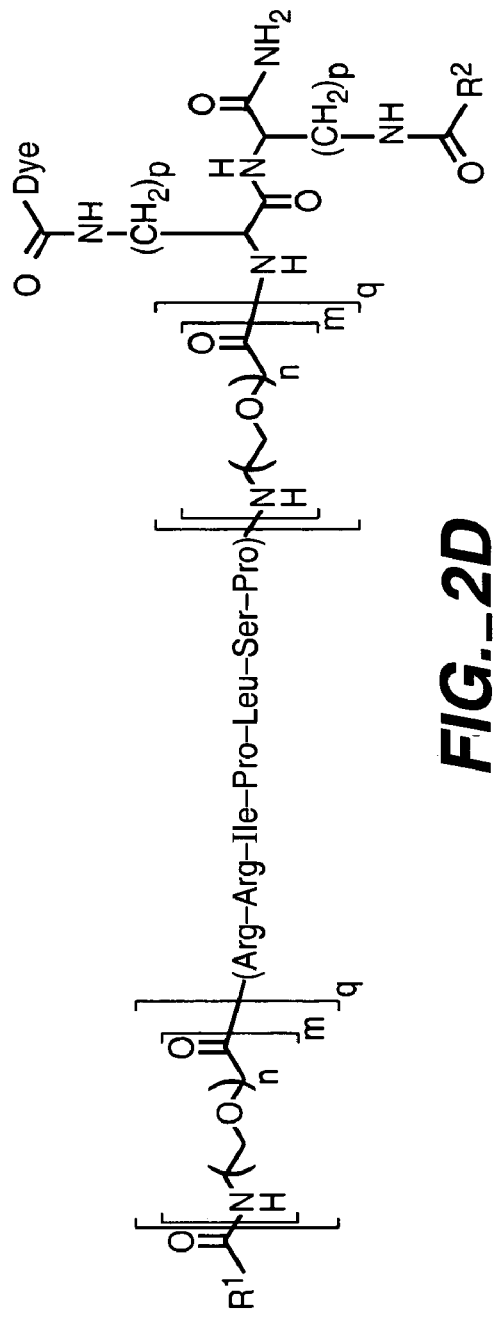
FIG._2D
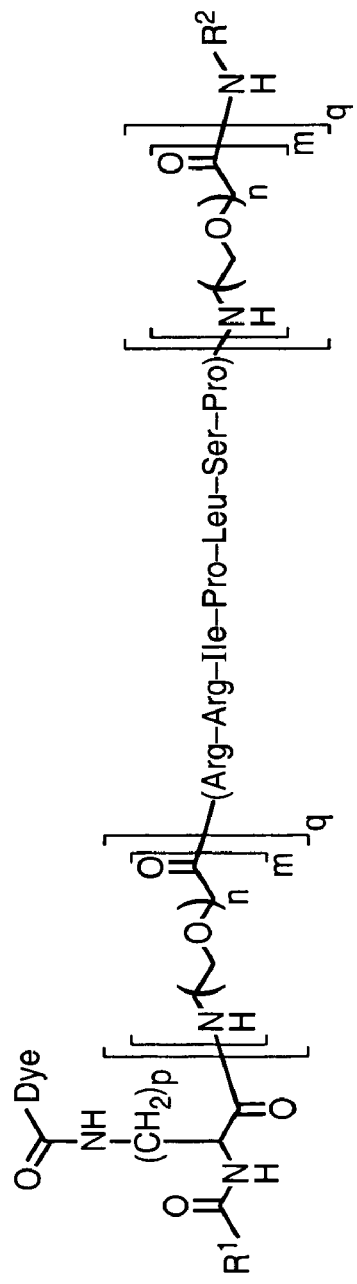
FIG._2E

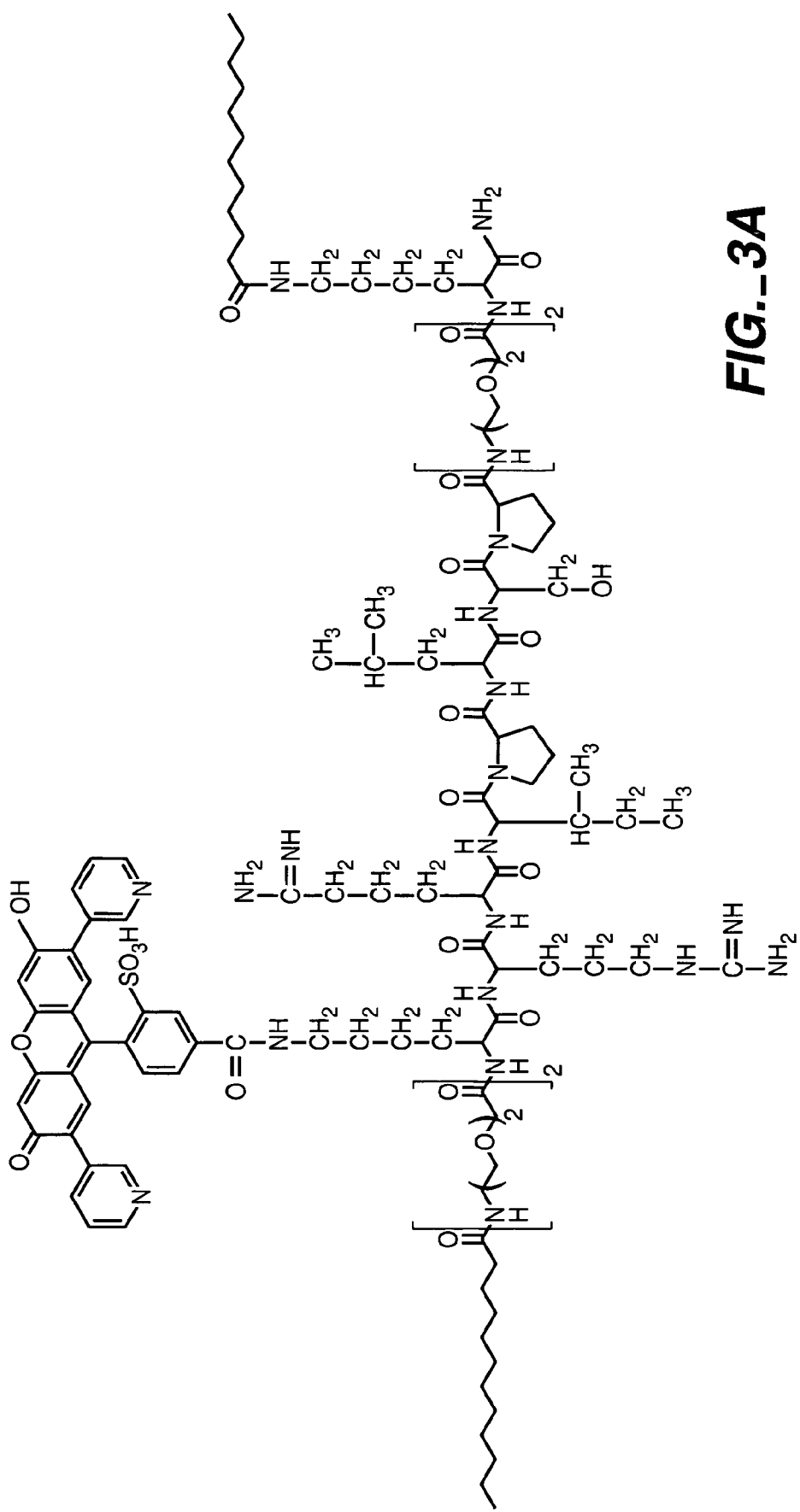
FIG._3A

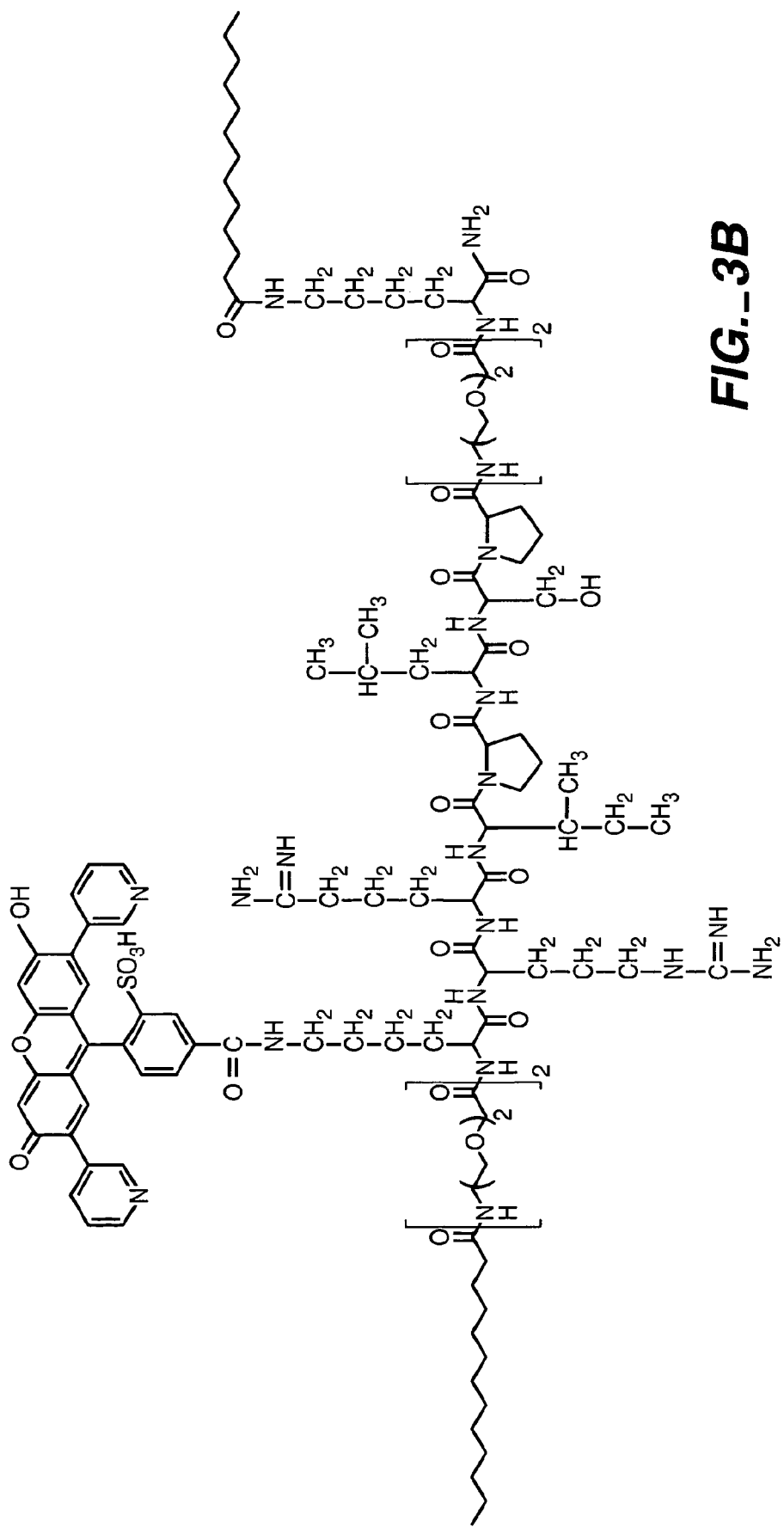
FIG._3B

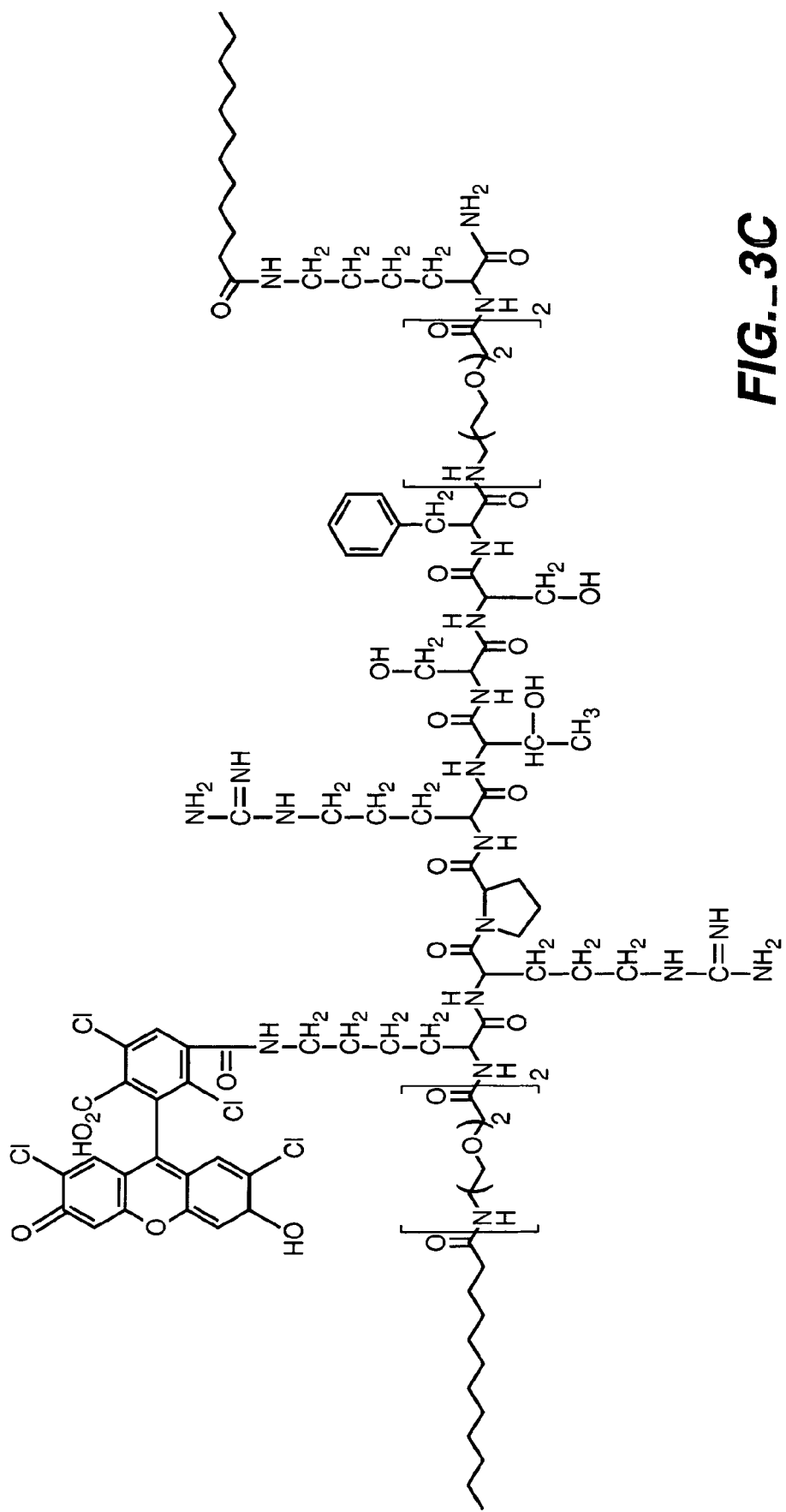
FIG._3C

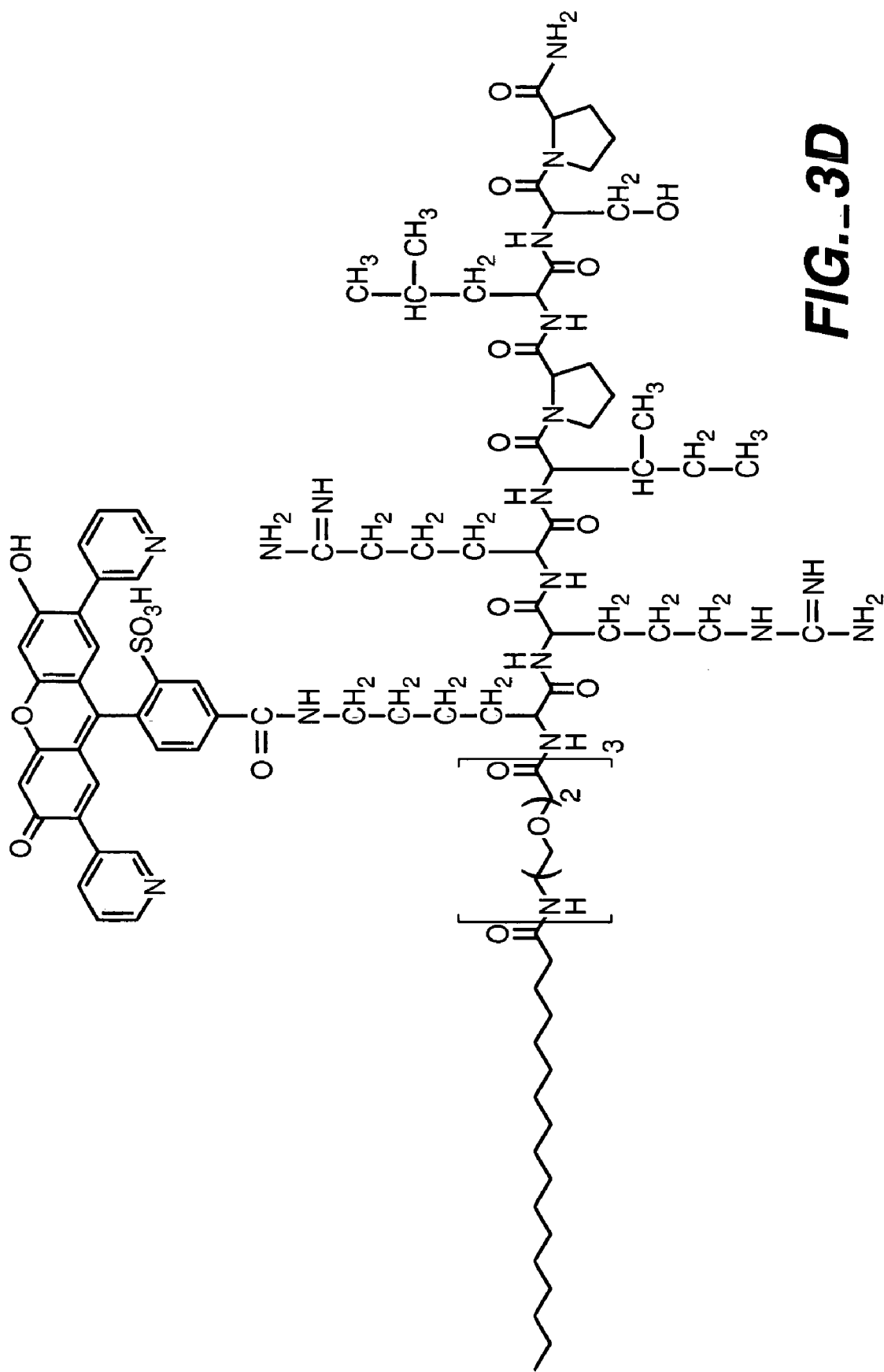
FIG._3D

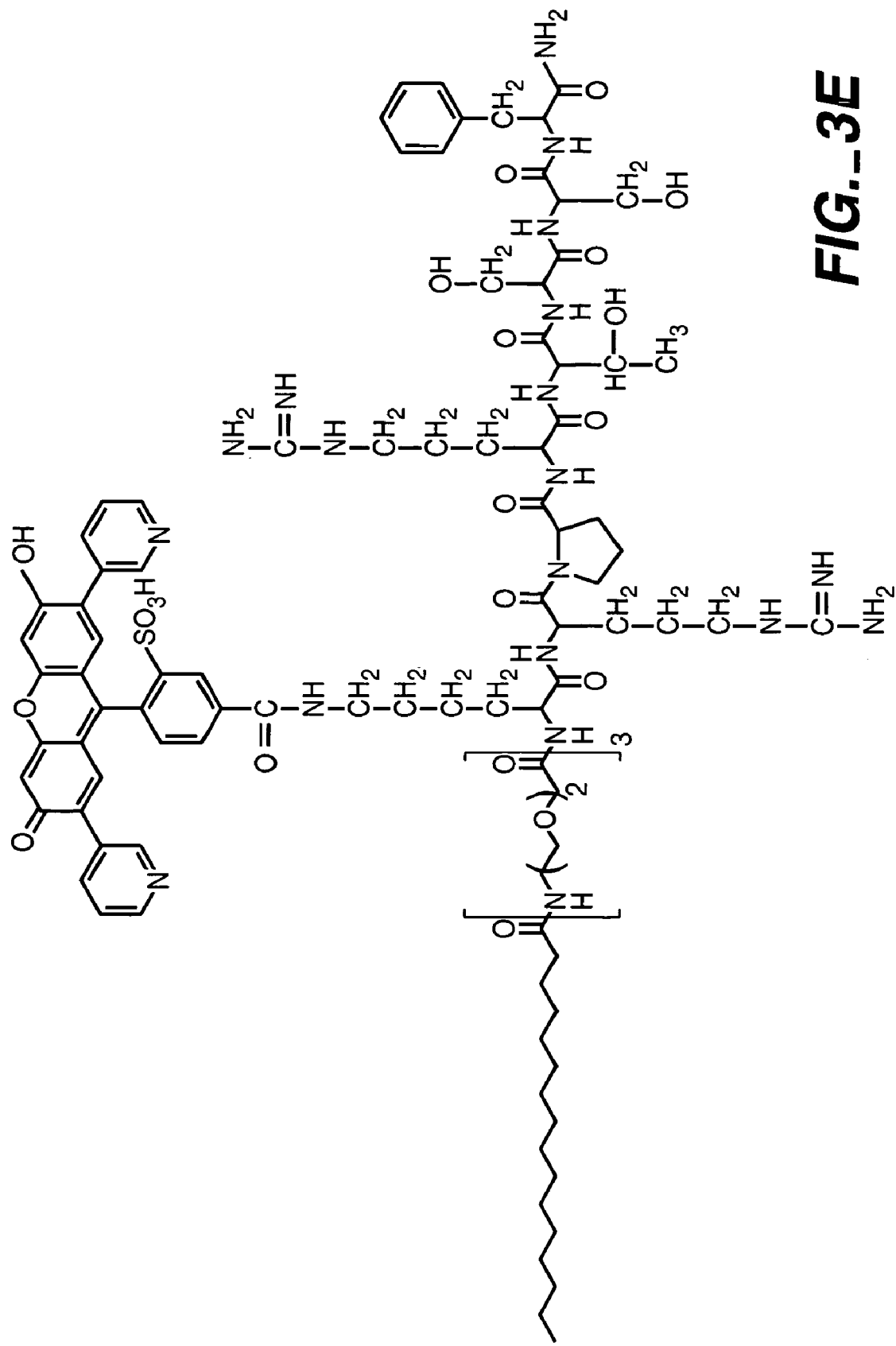
FIG._3E

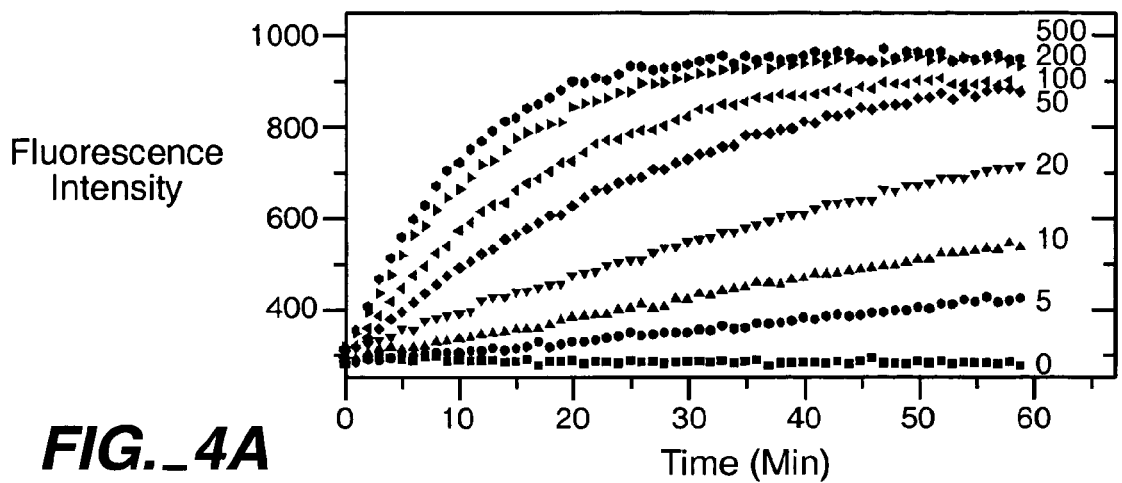
FIG._4A
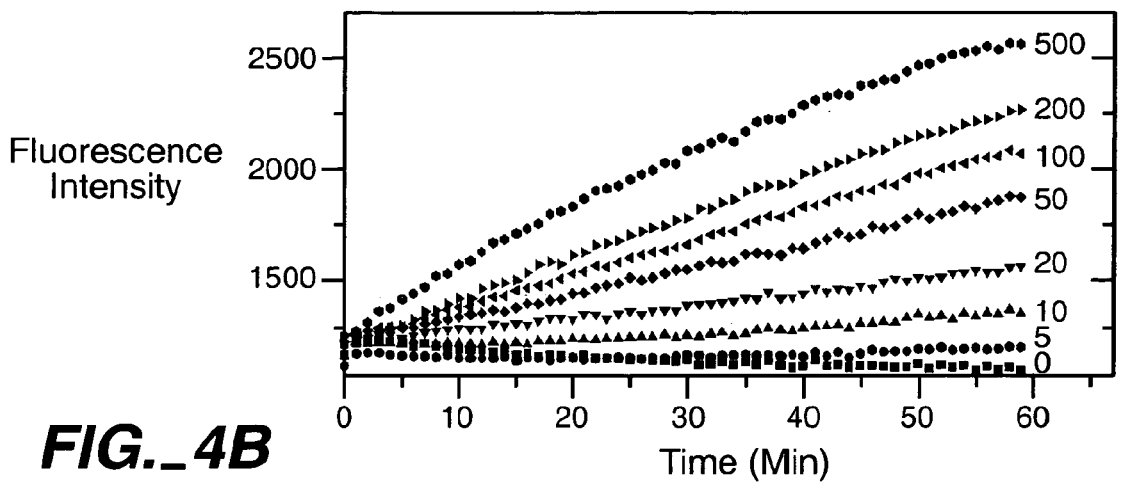
FIG._4B
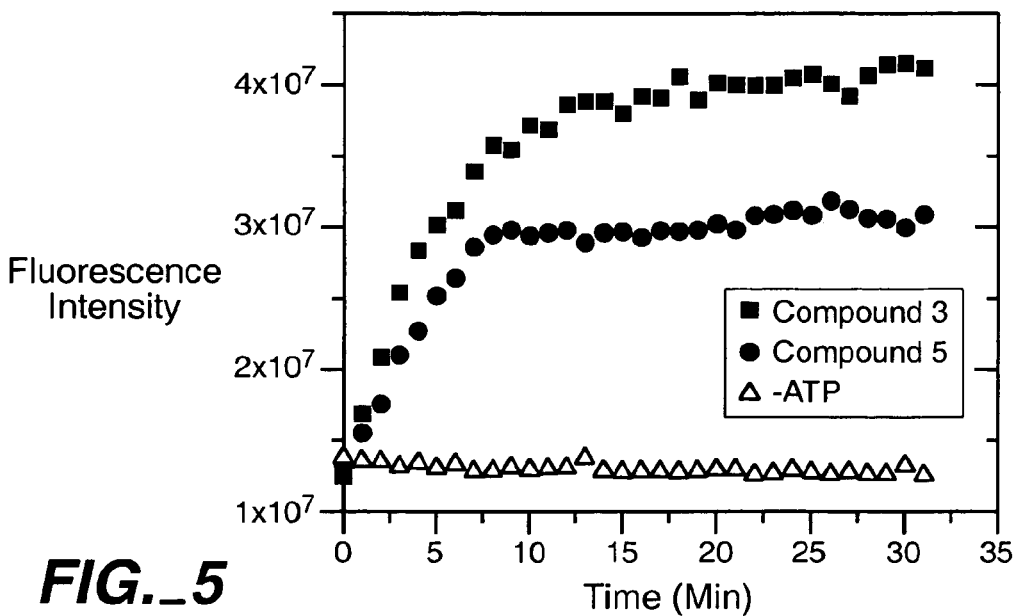
FIG._5

FLUOROGENIC KINASE ASSAYS AND SUBSTRATES

CROSS-REFERENCES TO RELATED APPLICATIONS

This application claims benefit under 35 U.S.C. § 119(e) to application Ser. No. 60/537,416, entitled "Fluorogenic Kinase Assays and Substrates," filed Jan. 16, 2004, the disclosure of which is incorporated herein by reference in its entirety.

FIELD

The present disclosure relates to fluorescent compositions and methods for detecting or characterizing enzymes and various uses thereof.

INTRODUCTION

Enzyme assays are important tools for studying and detecting enzymes for biological and industrial applications. In living organisms, enzymes perform a multitude of tasks, such as synthesis and replication of nucleic acids, modification, and degradation of polypeptides, synthesis of metabolites, and many other functions. Enzymes are also used in industry for many purposes, such as proteases used in laundry detergents, metabolic enzymes to make specialty chemicals such as amino acids and vitamins, and chirally specific enzymes to prepare enantiomerically pure drugs. In medical testing, enzymes are important indicators of the health or disease of human patients.

Although numerous approaches have been developed for assaying enzymes, there is still a great need to find new assay designs that can be used to inexpensively and conveniently detect and characterize a wide variety of enzymes. For example, protein kinases constitute a large class of enzymes that mediate a vast number of fundamental cellular processes. The recent availability of a nearly complete sequence for the human genome has now made possible the identification of many protein kinase candidates that will require years of research to uncover their various metabolic roles (see for example J. C. Venter et al., Science 291:1304-1351 (2001)). Such studies could be significantly facilitated by new assays that are suitable for high throughput screening. However, currently available assay protocols are inconvenient, expensive, or have other deficiencies.

SUMMARY

In one aspect, the disclosure provides methods for detecting the phosphorylation activity of one or more protein kinases in a sample. In some embodiments, a mixture is provided comprising a sample and at least one kinase substrate, wherein the kinase substrate comprises (a) a protein kinase recognition moiety containing at least one unphosphorylated residue that is capable of being phosphorylated by a protein kinase, (b) two or more hydrophobic moieties, and (c) a fluorescent moiety. The mixture is subjected to conditions effective to allow phosphorylation of the unphosphorylated residue when a protein kinase is present in the sample, thereby increasing a fluorescent signal produced by the fluorescent moiety. Detection of an increase in a fluorescent signal indicates the presence of a protein kinase in the sample.

The protein kinases to be detected can be any protein kinase known in the art. For example, in some embodiments, the protein kinase comprises protein kinase A. In some embodiments, the protein kinase comprises protein kinase C. In some embodiments, the protein kinase comprises protein kinase candidate, and a method is used to confirm and/or characterize the kinase activity of the candidate.

The protein kinase substrate can be designed to be reactive with a particular protein kinase or a group of protein kinases, or it can be designed to determine substrate specificity and/or other catalytic features, such as determining a value for kcat or Km. The unphosphorylated residue in the protein kinase recognition moiety may be any group that is capable of being phosphorylated by a protein kinase. In other embodiments, for example, the residue is a tyrosine residue. In some embodiments, the residue is a serine residue. In still other embodiments, the residue is a threonine residue. In other embodiments, the protein kinase recognition moiety can comprise more than one residue capable of being phosphorylated. The residues may be the same, some of them may be the same and others different, or they may all differ from one another.

In addition to having one or more unphosphorylated residues capable of being phosphorylated, the recognition moiety may include additional amino acid residues (or analogs thereof) that facilitate binding specificity, affinity, and/or rate of phosphorylation by the protein kinase(s) to be detected. In some embodiments, the recognition moiety comprises at least 3, 4, 5, 6 or 7 amino acid residues.

The hydrophobic moieties are selected such that they, either individually or together, are capable of integrating the substrate into the micelle. In some embodiments, each hydrophobic moiety comprises a saturated or unsaturated hydrocarbon comprising from 6 to 30 carbon atoms. The hydrophobic moieties may be the same, some of them may be the same and others different, or they may all differ from one another. In some embodiments, each hydrophobic moiety comprises a hydrocarbon chain corresponding in structure to a hydrocarbon chain or "tail" of a naturally occurring fatty acid, lipid or phospholipid. Other embodiments are discussed further below. In some embodiments, the hydrophobic moieties facilitate an increase in fluorescence of the fluorescent moiety upon phosphorylation of the substrate that is greater than the amplitude of the increase that would be obtained with the same substrate structure either lacking a hydrophobic moiety or having a single hydrophobic moiety.

The substrate may be designed to have a particular net charge in the unphosphorylated state. In some embodiments, the substrate has a net charge of 0 (a net neutral charge), or about 0, when measured at pH 7.6, such that addition of a phosphate group yields a product having a net charge of negative 2. In other embodiments, the substrate has a net charge that is different from 0, such as −1, −2, or +1. In still other embodiments, the net charge of the substrate is 0 or less. In yet other embodiments, the net charge is −1 or less.

The fluorescent moiety may be any fluorescent entity that is operative in accordance with the present teachings. In some embodiments, the substrate comprises a single fluorescent moiety. In other embodiments, the substrate comprises two or more fluorescent moieties. Non-limiting examples of suitable fluorescent dyes that can comprise the fluorescent moiety(ies) include xanthene dyes such as fluorescein, sulfofluorescein and rhodamine dyes, cyanine dyes, bodipy dyes and squaraine dyes. Fluorescent moieties comprising other fluorescent dyes may also be used. In some embodiments, a fluorescent moiety comprises a fluorescein dye. In some embodiments, a fluorescent moiety comprises a sulfofluorescein dye. In some embodiments, a fluorescent moiety comprises a rhodamine dye.

The protein kinase recognition moiety, hydrophobic moieties, and fluorescent moiety(ies) are connected in any way that permits them to perform their respective functions. In some embodiments, the hydrophobic moieties are linked to each other through the protein kinase recognition moiety. In a specific example of these embodiments, the fluorescent moiety can be linked directly, or indirectly through a linker, to one of the hydrophobic moieties. For example, one of the hydrophobic moieties and a fluorescent moiety can be linked to one end of the protein kinase recognition moiety and the other hydrophobic moiety can be linked to the opposite end of the protein kinase recognition moiety. These linkages can be direct or indirect via a linker. In some embodiments, a multivalent linker can be used to link the hydrophobic moieties, the fluorescent moiety, and the recognition moiety. Other embodiments are discussed further below.

The mixture may include a single kinase substrate, or it may include a plurality of different kinase substrates. When the mixture includes a plurality of different kinase substrates, the substrates may differ from one another with respect to any one or more of their protein kinase recognition moieties, hydrophobic moieties and/or fluorescent moieties. As a specific example, the mixture can include two kinase substrates that differ from one another with respect to at least their fluorescent moieties. In some embodiments, the different fluorescent moieties can be selected such that their fluorescence spectra are resolvable from another. For example, the fluorescent moiety on a first kinase substrate may be selected to fluoresce in the green region of the spectrum and the fluorescent moiety on a second kinase substrate selected to fluoresce in the red region of the spectrum. In some embodiments, the kinase substrates can also differ from one another with respect to the specificities of their kinase recognition moieties, permitting the ability to carry out the method in a "multiplexed" fashion, where substrates specific for different kinases or kinase families are correlated with a particular fluorescence signal. When kinase substrates having such spectrally resolvable fluorescent moieties are used, the fluorescent moieties can be selected to have different absorbance or excitation spectra or maxima, or all or a subset may be selected to have similar absorbance or excitation spectra or maxima such that they can be simultaneously excited with a single excitation source.

When a plurality of different kinase substrates are used, although not required for operation, the fluorescent moieties on one or more of the substrates can be selected such that they quench the fluorescence of the fluorescent moieties on one or more of the other substrates when the moieties are in close proximity to one another such as, for example, by collisional quenching, fluorescence resonance energy transfer (FRET) or by another mechanism (or combination of mechanisms). As a specific example, the fluorescent moiety of a first kinase substrate can be selected that has an absorbance spectrum that sufficiently overlaps the emissions spectrum of the fluorescent moiety of a second kinase substrate such that the first fluorescent moiety substantially quenches the fluorescence of the second fluorescent moiety when the two are in close proximity to one another, such as when both kinase substrates are integrated into the same micelle. As another specific example, the fluorescent moieties of two (or more) different kinase substrates may be selected such that they quench the fluorescence of each other when in close proximity thereto.

Although not required for operation, the mixture may optionally include one or more amphipathic quenching molecules capable of quenching the fluorescence of a fluorescent moiety of a kinase substrate when the kinase substrate and the quenching molecule are in close proximity to one another, such as when the kinase substrate and quenching molecule are integrated into the same micelle. Such quenching molecules generally comprise a hydrophobic moiety capable of integrating the quenching molecule into a micelle and a quenching moiety. Specific embodiments of the hydrophobic moiety can include any of the hydrophobic moieties discussed in connection with the kinase substrates.

The quenching moiety can be any moiety capable of quenching the fluorescence of the fluorescent moiety of the kinase substrate. In some embodiments, the quenching moiety can itself be a fluorescent moiety that is capable of quenching the fluorescence of the fluorescent moiety of the kinase substrate when placed in close proximity thereto, such as, for example, by collisional quenching, fluorescence resonance energy transfer (FRET) or by another mechanism (or combination of mechanisms). As a specific example, the quenching moiety can be a fluorescent moiety having an absorbance spectrum that sufficiently overlaps the emissions spectrum of the fluorescent moiety of the kinase substrate such that the quenching moiety substantially quenches the fluorescence of the kinase substrate fluorescent moiety when the quenching moiety and fluorescent moiety of the kinase substrate are in close proximity to one another, such as when the quenching molecule and kinase substrate are integrated into the same micelle. In other embodiments, the quenching moiety is non-fluorescent. The quenching molecule can optionally include a protein kinase recognition moiety.

In another aspect, the disclosure provides methods for detecting a phosphatase activity of one or more protein phosphatases in a sample. In some embodiments of the methods, a mixture is provided comprising a sample and at least one phosphatase substrate, wherein the phosphatase substrate comprises (a) a phosphatase recognition moiety containing at least one phosphorylated residue that is capable of being dephosphorylated (hydrolyzed) by a phosphatase, (b) two or more hydrophobic moieties, and (c) a fluorescent moiety. The mixture is subjected to conditions effective to allow dephosphorylation of the phosphorylated residue when a phosphatase is present in the sample, thereby increasing a fluorescent signal produced by the fluorescent moiety. Detection of an increase in a fluorescent signal in the mixture indicates the presence of a phosphatase in the sample.

The phosphatase to be detected can be any phosphatase known in the art. Also, the phosphatase can be a phosphatase candidate, and the method used to confirm and/or characterize the phosphatase activity of the candidate.

The phosphatase substrate can be designed to be reactive with a particular phosphatase or a group of phosphatases, or it can be designed to determine substrate specificity and other catalytic features, such as determining a value for kcat or Km. The phosphorylated residue in the phosphatase recognition moiety may be any group that is capable of being dephosphorylated by a phosphatase. In some embodiments, for example, the residue is a phosphotyrosine residue. In other embodiments, the residue is a phosphoserine residue. In still other embodiments, the residue is a phosphothreonine residue.

In addition to having one or more phosphorylated residues capable of being dephosphorylated, the recognition moiety may include additional amino acid residues (or analogs thereof) that facilitate binding specificity, affinity, and/or rate of dephosphorylation by the phosphatase(s). In some embodiments, the recognition moiety comprises at least 3, 4, 5, 6 or 7 amino acid residues.

The hydrophobic moieties are selected such that they, either individually or together, are capable of integrating the substrate into the micelle. In some embodiments, each hydrophobic moiety comprises a saturated or unsaturated hydrocarbon comprising from 6 to 30 carbon atoms. The hydrophobic moieties may be the same, some of them may be the same and others different, or they may all differ from one another. Other embodiments are discussed further below. In some embodiments, each hydrophobic moiety comprises a hydrocarbon chain corresponding in structure to a hydrocarbon chain or "tail" of a naturally occurring fatty acid, lipid or phospholipid. In some embodiments, the hydrophobic moieties are chosen to facilitate an increase in fluorescence of the fluorescent moiety upon dephosphorylation of the substrate that is greater than the amplitude of the increase that would be obtained with the same substrate structure either lacking a hydrophobic moiety or having a single hydrophobic moiety.

The substrate may be designed to have a particular net charge in the phosphorylated state. In some embodiments, the substrate has a net charge of 0 (a net neutral charge), or about 0, when measured at pH 7.6, such that removal of a phosphate group yields a product having a net charge of +2. In other embodiments, the substrate has a net charge that is different from 0, such as +1, +2, or −1. In still other embodiments, the net charge of the substrate is 0 or greater. In yet other embodiments, the net charge is +1 or greater.

The fluorescent moiety of the phosphatase substrate may be any fluorescent entity that is operative in accordance with the present teachings. In some embodiments, the substrate comprises a single fluorescent moiety. In other embodiments, the substrate comprises two or more fluorescent moieties. Non-limiting examples of suitable fluorescent dyes that can comprise the fluorescent moiety(ies) include xanthene dyes such as fluorescein, sulfofluorescein and rhodamine dyes, cyanine dyes, bodipy dyes and squaraine dyes. Fluorescent moieties comprising other fluorescent dyes may also be used. In some embodiments, a fluorescent moiety comprises a fluorescein dye. In some embodiments, a fluorescent moiety comprises a sulfofluorescein dye. In some embodiments, a fluorescent moiety comprises a rhodamine dye.

The phosphatase recognition moiety, hydrophobic moieties, and fluorescent moiety are connected in any way that permits them to perform their respective functions, in a manner analogous to the design considerations discussed above with respect to the protein kinase substrates.

The mixture may include a single phosphatase substrate, or it may include a plurality of different phosphatase substrates. When the mixture includes a plurality of different phosphatase substrates, the substrates may differ from one another with respect to any one or more of their phosphatase recognition moieties, hydrophobic moieties and/or fluorescent moieties. As a specific example, the mixture can include two phosphatase substrates that differ from one another with respect to at least their fluorescent moieties. In some embodiments, the different fluorescent moieties can be selected such that their fluorescence spectra are resolvable from another. For example, the fluorescent moiety on a first phosphatase substrate may be selected to fluoresce in the green region of the spectrum and the fluorescent moiety on a second phosphatase substrate selected to fluoresce in the red region of the spectrum. In some embodiments, the phosphatase substrates can also differ from one another with respect to the specificities of their phosphatase recognition moieties, permitting the ability to carry out the method in a "multiplexed" fashion, where substrates specific for different phosphatase or phosphatase families are correlated with a particular fluorescence signal. When phosphatase substrates having such spectrally resolvable fluorescent moieties are used, the fluorescent moieties can be selected to have different absorbance or excitation spectra or maxima, or all or a subset may be selected to have similar absorbance or excitation spectra or maxima such that they can be simultaneously excited with a single excitation source.

When a plurality of different phosphatase substrates are used, although not required for operation, the fluorescent moieties on one or more of the substrates can be selected such that they quench the fluorescence of the fluorescent moieties on one or more of the other substrates when the moieties are in close proximity to one another such as, for example, by collisional quenching, fluorescence resonance energy transfer (FRET) or by another mechanism (or combination of mechanisms). As a specific example, the fluorescent moiety of a first phosphatase substrate can be selected that has an absorbance spectrum that sufficiently overlaps the emissions spectrum of the fluorescent moiety of a second phosphatase substrate such that the first fluorescent moiety substantially quenches the fluorescence of the second fluorescent moiety when the two are in close proximity to one another, such as when both phosphatase substrates are integrated into the same micelle. As another specific example, the fluorescent moieties of two (or more) different phosphatase substrates may be selected such that they quench the fluorescence of each other when in close proximity thereto.

Although not required for operation, the mixture may optionally include one or more amphipathic quenching molecules capable of quenching the fluorescence of a fluorescent moiety of a phosphatase substrate when the phosphatase substrate and the quenching molecule are in close proximity to one another, such as when the phosphatase substrate and quenching molecule are integrated into the same micelle. Such quenching molecules generally comprise a hydrophobic moiety capable of integrating the quenching molecule into a micelle and a quenching moiety. Specific embodiments of the hydrophobic moiety can include any of the hydrophobic moieties discussed in connection with the phosphatase substrates.

The quenching moiety can be any moiety capable of quenching the fluorescence of the fluorescent moiety of the phosphatase substrate. In some embodiments, the quenching moiety can itself be a fluorescent moiety that is capable of quenching the fluorescence of the fluorescent moiety of the phosphatase substrate when placed in close proximity thereto, such as, for example, by collisional quenching, fluorescence resonance energy transfer (FRET) or by another mechanism (or combination of mechanisms). As a specific example, the quenching moiety can be a fluorescent moiety having an absorbance spectrum that sufficiently overlaps the emissions spectrum of the fluorescent moiety of the phosphatase substrate such that the quenching moiety substantially quenches the fluorescence of the phosphatase substrate fluorescent moiety when the quenching moiety and fluorescent moiety of the phosphatase substrate are in close proximity to one another, such as when the quenching molecule and phosphatase substrate are integrated into the same micelle. In other embodiments, the quenching moiety is non-fluorescent. The quenching molecule can optionally include a phosphatase recognition moiety.

In another aspect, the present disclosure provides methods for detecting or measuring an enzyme activity. In some embodiments of the methods, a mixture comprising a sample and a substrate for the enzyme is provided. The substrate comprises (a) an enzyme recognition moiety that contains a chemical reaction site that is capable of being modified by the enzyme in a manner that changes the net charge of the substrate, (b) two or more hydrophobic moieties, and (c) a fluorescent moiety. The mixture is subjected to conditions effective to allow the enzyme to modify the chemical reaction site to produce a fluorescently detectable product that contains the modified enzyme recognition moiety, the hydrophobic moieties, and the fluorescent moiety, thereby increasing a fluorescent signal produced by the fluorescent moiety. Detection of an increase in fluorescent signal indicates the presence of the enzyme in the sample.

In some embodiments, the enzyme is a protein kinase. In other embodiments, the enzyme is a protein phosphatase.

In some embodiments, the enzyme recognition moiety comprises a polypeptide segment that contains a group that is chemically altered by the enzyme during the assay to cause an increased fluorescent signal. In some embodiments, the recognition moiety comprises at least 3, 4, 5, 6 or 7 amino acid residues.

The hydrophobic moieties are selected such that they, either individually or together, are capable of integrating the substrate into the micelle. In some embodiments, each hydrophobic moiety comprises a saturated or unsaturated hydrocarbon comprising from 6 to 30 carbon atoms. The hydrophobic moieties may be the same, some of them may be the same and others different, or they may all differ from one another. Other embodiments are discussed further below. In some embodiments, each hydrophobic moiety comprises a hydrocarbon chain corresponding in structure to a hydrocarbon chain or "tail" of a naturally occurring fatty acid, lipid or phospholipid. In some embodiments, the hydrophobic moieties are chosen to facilitate an increase in fluorescence of the fluorescent moiety upon enzyme reaction with the substrate that is greater than the amplitude of the increase that would be obtained with the same substrate structure lacking the hydrophobic moieties.

The substrate may be designed to have a particular net charge before reaction with the enzyme. In some embodiments, the substrate has a net charge of 0 (a net neutral charge), or about 0, when measured at pH 7.6. In some embodiments, the substrate has a net charge that is different from 0, such as −1, −2, or +1 or +2. In other embodiments, the net charge of the substrate is 0 or less. In still other embodiments, the net charge is −1 or less. In yet other embodiments, the net charge of the substrate is 0 or greater or +1 or greater.

In some embodiments, the enzyme reacts with the substrate to add or remove a group that causes a change in the charge of the substrate. For example, reaction of the substrate with the enzyme can cause an increase in the amplitude of the net charge of the substrate, so that the product has a greater negative charge than the substrate or a greater positive charge than the substrate.

The fluorescent moiety may be any fluorescent entity that is operative in accordance with the present teachings. In some embodiments, the substrate comprises a single fluorescent moiety. In other embodiments, the substrate comprises two or more fluorescent moieties. Non-limiting examples of suitable fluorescent dyes that can comprise the fluorescent moiety(ies) include xanthene dyes such as fluorescein, sulfofluorescein and rhodamine dyes, cyanine dyes, bodipy dyes and squaraine dyes. Fluorescent moieties comprising other fluorescent dyes may also be used. In some embodiments, a fluorescent moiety comprises a fluorescein dye. In some embodiments, a fluorescent moiety comprises a sulfofluorescein dye. In some embodiments, a fluorescent moiety comprises a rhodamine dye.

The enzyme recognition moiety, hydrophobic moieties, and fluorescent moiety are connected in any way that permits them to perform their respective functions. In some embodiments, the hydrophobic moieties are linked to each other through the protein kinase recognition moiety. In a specific example of these embodiments, the fluorescent moiety can be linked directly, or indirectly through a linker, to one of the hydrophobic moieties. For example, one of the hydrophobic moieties and a fluorescent moiety can be linked to one end of the protein kinase recognition moiety and the other hydrophobic moiety can be linked to the opposite end of the protein kinase recognition moiety. These linkages can be direct or indirect via a linker. In some embodiments, a multivalent linker can be used to link the hydrophobic moieties, the fluorescent moiety, and the protein kinase recognition moiety. Other embodiments are discussed further below.

In some embodiments, the action of the enzyme is effective to produce a product that is more fluorescent than the substrate in the reaction mixture, such that the enzyme recognition moiety, hydrophobic moieties, and fluorescent moiety remain present in (are not cleaved from) the product.

The mixture may include a single enzyme substrate or a plurality of enzyme substrates, in a manner analogous to that described above in connection with kinase substrates and phosphatase substrates. The mixture may also include one or more quenching molecules, as discussed above.

The disclosure also includes fluorescent substrates and compositions and kits containing them, as discussed further herein.

The methods and compositions described herein may also be used to detect, screen for, and/or characterize substrates, inhibitors, activators, or modulators of enzyme activity, as discussed further herein.

These and other features of the various embodiments herein will become more apparent from the detailed description.

BRIEF DESCRIPTION OF THE DRAWINGS

The skilled artisan will understand that the drawings, described below, are for illustration purposes only. The drawings are not intended to limit the scope of the present teachings in any way.

FIG. 1 illustrates an exemplary embodiment of a kinase substrate comprising two hydrophobic moieties connected to opposite ends of a protein kinase recognition moiety.

FIGS. 2A-2E illustrate additional exemplary embodiments of kinase substrates comprising two hydrophobic moieties (SEQ ID NO: 20).

FIGS. 3A-C illustrate exemplary embodiments of kinase substrates comprising two hydrophobic moieties connected to either end of a protein kinase recognition moiety.

FIGS. 3D-3E illustrate embodiments of kinase substrates comprising one hydrophobic moiety for comparison purposes.

FIG. 4A shows the rate of reaction for a kinase substrate i.e., $C_{12}$OOK(Dye 2)RRIPLSPOOK($C_{12}$)NH$_2$ (peptide disclosed as SEQ ID NO: 20) (2 µM) comprising two hydrophobic moieties for protein kinase p38βII (14 nM) for several concentrations of ATP (0, 5, 10, 20, 50, 100, 200, and 500 µM).

FIG. 4B shows the rate of reaction for a kinase substrate, i.e. $C_{16}OOK(Dye\ 2)RRIPLSPNH_2$ (peptide disclosed as SEQ ID NO: 20) (4 µM) comprising one hydrophobic moiety for protein kinase p38βII(14 nM) for several concentrations of ATP (0, 5, 10, 20, 50, 100, 200, and 500 µM).

FIG. 5 shows the rate of reaction for a kinase substrate comprising two hydrophobic moieties, LL21-120B (i.e. $C_{11}OOK(tet)RPRTSSFOOK(C_{11})NH_2$, peptide disclosed as SEQ ID NO: 17), 8 µM) versus a kinase substrate comprising one hydrophobic moiety, Aktv1.0 (i.e. $C_{15}OOK(Dye\ 2)RPRTSSFNH_2$, peptide disclosed as SEQ ID NO: 17), 8 µM) for protein kinase Akt3/PKBγ (6 nM) at an ATP concentration of 100 µM.

DESCRIPTION OF VARIOUS EMBODIMENTS

I. Definitions

Unless stated otherwise, the following terms and phrases used herein are intended to have the following meanings:

"Detect" and "detection" have their standard meaning, and are intended to encompass detection, measurement and/or characterization of a selected enzyme or enzyme activity. For example, enzyme activity may be "detected" in the course of detecting, screening for, or characterizing inhibitors, activators, and modulators of the enzyme activity.

"Fatty Acid" has its standard meaning and is intended to refer to a long-chain hydrocarbon carboxylic acid in which the hydrocarbon chain is saturated, mono-unsaturated or polyunsaturated. The hydrocarbon chain may be linear, branched or cyclic, or may comprise a combination of these features, and may be unsubstituted or substituted. Fatty acids typically have the structural formula R—C(O)OH, where R is a substituted or unsubstituted, saturated, mono-unsaturated or polyunsaturated hydrocarbon comprising from 6 to 30 carbon atoms which has a structure that is linear, branched, cyclic or a combination thereof.

"Micelle" has its standard meaning and is intended to refer to an aggregate formed by amphipathic molecules in water or an aqueous environment such that their polar ends or portions are in contact with the water or aqueous environment and their nonpolar ends or portions are in the interior of the aggregate. A micelle can take any shape or form, including but not limited to, a non-lamellar "detergent-like" aggregate that does not enclose a portion of the water or aqueous environment, or a unilamellar or multilamellar "vesicle-like" aggregate that encloses a portion of the water or aqueous environment, such as, for example, a liposome.

"Quench" has its standard meaning and is intended to refer to a measurable reduction in the fluorescence intensity of a fluorescent group or moiety as measured at a specified wavelength, regardless of the mechanism by which the reduction is achieved. As specific examples, the quenching may be due to molecular collision, energy transfer such as FRET, a change in the fluorescence spectrum (color) of the fluorescent group or moiety or any other mechanism (or combination of mechanisms). The amount of the reduction is not critical and may vary over a broad range. The only requirement is that the reduction be measurable by the detection system being used. Thus, a fluorescence signal is "quenched" if its intensity at a specified wavelength is reduced by any measurable amount. A fluorescence signal is "substantially quenched" if its intensity at a specified wavelength is reduced by at least 50%, for example by 50%, 60%, 70%, 75%, 80%, 85%, 90%, 95%, 96%, 97%, 98%, 99% or even 100%.

Polypeptide sequences are provided with an orientation (left to right) of the N terminus to C terminus, with amino acid residues represented by the standard 3-letter or 1-letter codes (e.g., Stryer, L., *Biochemistry*, 2$^{nd}$ Ed., W.H. Freeman and Co., San Francisco, Calif., page 16 (1981)).

II. Enzyme Substrate Compositions

Provided herein are enzyme substrates that can be designed to detect any of a large variety of different enzymes. The substrates comprise two or more hydrophobic moieties capable of integrating the substrate into a micelle. The substrates also contain one or more fluorescent moiety(ies) whose fluorescence increases when the enzyme substrate is reacted with an enzyme of interest, without requiring a quenching group to suppress the fluorescence of the fluorescent moiety prior to reaction of the substrate with the enzyme. Advantageously, the substrates described herein can be used in a continuous monitoring phase, in real time, to allow the user to rapidly determine whether enzyme activity is present in the sample, and optionally, the amount or specific activity of the enzyme.

By way of illustration, the substrates and methods are first discussed below with reference to protein kinases as exemplary enzymes to be detected or characterized. In addition to playing important biochemical roles, protein kinases are also useful for illustrating enzymes that cause an increase in the net charge of an enzyme substrate by adding a phosphate group to a hydroxyl group to form a phosphorylated substrate. Under physiological conditions, i.e. pH 7.6, phosphorylation of the substrate causes the addition of two negative charges, for a net change in charge of –2. Enzymes that carry out the opposite reaction, protein phosphatases, are also discussed, which cause a net increase in charge of +2 under physiological conditions, i.e. pH 7.6. In either case, the amplitude of the net charge on the enzyme substrate is increased. For example, upon phosphorylation of an enzyme substrate as described above, the amplitude of the net negative charge on the enzyme substrate is increased by –2. On the other hand, upon dephosphorylation of an enzyme substrate by a phosphatase, the amplitude of the net positive charge on the enzyme substrate is increased by +2.

In some embodiments, a kinase substrate for detecting or characterizing one or more protein kinases in a sample is provided. In one exemplary class of compounds, the kinase substrate comprises at least (a) a protein kinase recognition moiety containing at least one unphosphorylated residue that is capable of being phosphorylated by a protein kinase, (b) two or more hydrophobic moieties capable of integrating the substrate into a micelle, and (c) one or more fluorescent moiety(ies).

The protein kinase recognition moiety generally includes at least one amino acid side chain containing a group that is capable of being phosphorylated by a protein kinase. In some embodiments, the phosphorylatable group is a hydroxyl group. Usually, the hydroxyl group is provided as part of a side chain in a tyrosine, serine, or threonine residue, although any other natural or non-natural amino acid side chain or other entity containing a phosphorylatable hydroxyl group can be used. The phosphorylatable group can also be a nitrogen atom, such as the nitrogen atom in the epsilon amino group of lysine, an imidazole nitrogen atom of histidine, or a guanidinium nitrogen atom of arginine. The phosphorylatable group can also be a carboxyl group in an asparate or glutamate residue.

The protein kinase recognition moiety may further comprise a segment, typically a polypeptide segment, that contains one or more subunits or residues (in addition to the phosphorylatable residue) that impart identifying features to the substrate to make it compatible with the substrate specificity of the protein kinase(s) to be detected or characterized.

A wide variety of protein kinases have been characterized over the past several decades, and numerous classes have been identified (see, e.g., S. K. Hanks et al., Science 241: 42-52 (1988); B. E. Kemp and R. B. Pearson, Trends Biochem. Sci. 15:342-346 (1990); S. S. Taylor et al., Ann. Rev. Cell Biol. 8:429-462 (1992); Z. Songyang et al., Current Biology 4:973-982 (1994); and Chem. Rev. 101:2209-2600, "Protein Phosphorylation and Signaling" (2001)). Exemplary classes of protein kinases include cAMP-dependent protein kinases (also called the protein kinase A family, A-proteins, or PKA's), cGMP-dependent protein kinases, protein kinase C enzymes (PKC's, including calcium dependent PKC's activated by diacylglycerol), $Ca^{2+}$/calmodulin-dependent protein kinase I or II, protein tyrosine kinases (e.g., PDGF receptor, EGF receptor, and Src), mitogen activated protein (MAP) kinases (e.g., ERK1, KSS1, and MAP kinase type I), cyclin-dependent kinases (CDk's, e.g., Cdk2 and Cdc2), and receptor serine kinases (e.g., TGF-β). Exemplary consensus sequences for various protein kinases are shown in Table 1, below. These various consensus sequences can be used to design protein kinase recognition moieties having desired specificities for particular kinases and/or kinase families.

Protein kinase recognition moieties having desired specificities for particular kinases and/or kinase families can also be designed, for example, using the methods and/or exemplary sequences described in Brinkworth et al., Proc. Natl. Acad. Sci. USA 100(1):74-79 (2003).

TABLE 1

| Symbol | Description | Consensus Sequence[a] |
|---|---|---|
| PKA | cAMP-dependent | -R-R-X-S/T-Z- (SEQ ID NO:1) |
| PhK | phosphorylase kinase | -R-X-X-S/T-F-F- (SEQ ID NO:2) |
| cdk2 | cyclin-dependent kinase-2 | -S/T-P-X-R/K (SEQ ID NO:3) |
| ERK2 | extracellular-regulated kinase-2 | -P-X-S/T-P- (SEQ ID NO:4) |
| PKC | protein kinase C | KKKKRFSFK[b] (SEQ ID NO:5)<br>XRXXSXRX (SEQ ID NO:6) |
| CaMKI | $Ca^{2+}$/calmodulin-dependent protein kinase I | LRRLSDSNF[c] (SEQ ID NO:7) |
| CaMKII | $Ca^{2+}$/calmodulin-dependent protein kinase II | KKLNRTLTVA[d] (SEQ ID NO:8) |
| c-Src | cellular form of Rous sarcoma virus transforming agent | -E-E-I-Y-E/G-X-F- (SEQ ID NO:9) |
| v-Fps | transforming agent of Fujinami sarcoma virus | -E-I-Y-E-X-I/V- (SEQ ID NO:10) |
| Csk | C-terminal Src kinase | -I-Y-M-F-F-F- (SEQ ID NO:11) |
| InRK | Insulin receptor kinase | -Y-M-M-M- (SEQ ID NO:12) |
| EGFR | EGF receptor | -E-E-E-Y-F- (SEQ ID NO:13) |

[a]See, for example, B. E. Kemp and R. B. Pearson, Trends Biochem. Sci. 15: 342-346 (1990); Z. Songyang et al., Current Biology 4: 973-982 (1994); J. A. Adams, Chem Rev. 101: 2272 (2001) and references cited therein; X means any amino acid residue, "/" indicates alternate residues; and Z is a hydrophobic amino acid, such as valine, leucine or isoleucine
[b]Graff et al., J. Biol. Chem. 266: 14390-14398 (1991)
[c]Lee et al., Proc. Natl. Acad. Sci. 91: 6413-6417 (1994)
[d]Stokoe et al., Biochem. J. 296: 843-849 (1993)

Typically, the protein kinase recognition sequence comprises a sequence of L-amino acid residues. However, any of a variety of amino acids with different backbone or sidechain structures can also be used, such as: D-amino acid polypeptides, alkyl backbone moieties joined by thioethers or sulfonyl groups, hydroxy acid esters (equivalent to replacing amide linkages with ester linkages), replacing the alpha carbon with nitrogen to form an aza analog, alkyl backbone moieties joined by carbamate groups, polyethyleneimines (PEIs), and amino aldehydes, which result in polymers composed of secondary amines. A more detailed backbone list includes N-substituted amide (—CON(R)— replaces —CONH— linkages), esters (—CO$_2$—), keto-methylene (—COCH$_2$—) methyleneamino (—CH$_2$NH—), thioamide (—CSNH—), phosphinate (—PO$_2$RCH$_2$—), phosphonamidate and phosphonamidate ester (—PO$_2$RNH$_2$), retropeptide (—NHC(O)—), trans-alkene (—CR=CH—), fluoroalkene (e.g.; —CF=CH—), dimethylene (—CH$_2$CH$_2$—), thioether (e.g.; —CH$_2$SCH$_2$—), hydroxyethylene (—CH(OH)CH$_2$—), methyleneoxy(—CH$_2$O—), tetrazole (—CN$_4$—), retrothioamide (—NHC(S)—), retroreduced (—NHCH$_2$—), sulfonamido (—SO$_2$NH—), methylenesulfonamido (—CHRSO$_2$NH—), retrosulfonamide (—NHS(O$_2$)—), and peptoids (N-substituted glycines), and backbones with malonate and/or gem-diaminoalkyl subunits, for example, as reviewed by M. D. Fletcher et al., Chem. Rev. 98:763 (1998) and the references cited therein. Peptoid backbones (N-substituted glycines) can also be used (e.g., H. Kessler, Angew. Chem. Int. Ed. Engl. 32:543 (1993); R. N. Zuckermann, Chemtracts-Macromol. Chem. 4:80 (1993); and Simon et al., Proc. Natl. Acad. Sci. 89:9367 (1992)).

The recognition moiety may comprise a polypeptide segment containing the group or residue that is to be phosphorylated. In some embodiments, the polypeptide segment has a polypeptide length equal to or less than 30 amino acid residues, 25 residues, 20 residues, 15 residues, 10 residues, or 5 residues. In other embodiments, the polypeptide segment has a polypeptide length in a range of 3 to 30 residues, or 3 to 25 residues, or 3 to 20 residues, or 3 to 15 residues, or 3 to 10 residues, or 3 to 5 residues, or 5 to 30 residues, or 5 to 25 residues, or 5 to 20 residues, or 5 to 15 residues, or 5 to 10 residues, or 10 to 30 residues, or 10 to 25 residues, or 10 to 20 residues, or 10 to 15 residues. In other embodiments, the polypeptide segment contains 3 to 30 amino acid residues, or 3 to 25 residues, or 3 to 20 residues, or 3 to 15 residues, or 3 to 10 residues, or 3 to 5 residues, or 5 to 30 residues, or 5 to 25 residues, or 5 to 20 residues, or 5 to 15 residues, or 5 to 10 residues, or 10 to 30 residues, or 10 to 25 residues, or 10 to 20 residues, or 10 to 15 residues. In other embodiments, the polypeptide segment contains at least 3, 4, 5, 6 or 7 amino acid residues.

The protein kinase substrates typically comprise two or more hydrophobic moieties capable of anchoring or integrating the kinase substrates into the micelle. The exact numbers, lengths, sizes and/or composition of the hydrophobic moieties can be varied. In embodiments employing two or more hydrophobic moieties, each hydrophobic moiety may be the same, or some or all of the hydrophobic moieties may differ.

In some embodiments, the hydrophobic moieties comprise a substituted or unsubstituted hydrocarbon of sufficient hydrophobic character (e.g., length and/or size) to cause the substrate molecule to become integrated or incorporated into a micelle when the substrate molecule is placed in an aqueous environment at a concentration above a micelle-forming threshold, such as at or above its critical micelle concentration (CMC). In other embodiments, the hydrophobic moieties comprise a substituted or unsubstituted hydrocarbon comprising from 6 to 30 carbon atoms, or from 6 to 25 carbon atoms, or from 6 to 20 carbon atoms, or from 6 to 15 carbon atoms, or from 8 to 30 carbon atoms, or from 8 to 25 carbon atoms, or from 8 to 20 carbon atoms, or from 8 to 15 carbon atoms, or from 12 to 30 carbon atoms, or from 12 to 25 carbon atoms, or from 12 to 20 carbon atoms. The hydrocarbon may be linear, branched, cyclic, or any combination thereof, and may optionally include one or more of the same or different substituents. Exemplary linear hydrocarbon groups comprise C6, C7, C8, C9, C10, C11, C12, C13, C14, C15, C16, C17, C18, C19, C20, C22, C24, and C26 alkyl chains.

In some embodiments, the hydrophobic moieties are fully saturated. In some embodiments, the hydrophobic moieties can comprise one or more carbon-carbon double bonds which may be, independently of one another, in the cis or trans configuration, and/or one or more carbon-carbon triple bonds. In some cases, the hydrophobic moieties may have one or more cycloalkyl groups, or one or more aryl rings or arylalkyl groups, such as one or two phenyl rings.

In some embodiments, the hydrophobic moieties are nonaromatic moieties that do not have a cyclic aromatic pi electron system. In some embodiments, if the hydrophobic moieties contain one or more unsaturated carbon-carbon bonds, those carbon-carbon bonds are not conjugated. In other embodiments, the structure of the hydrophobic moieties is incapable of interacting with the fluorescent moiety, by a FRET or stacking interaction, to quench fluorescence of the fluorescent moiety. Also encompassed herein are embodiments that involve a combination of any two or more of the foregoing embodiments. Optimization testing can be done by making several signal compounds having different hydrophobic moieties.

In some embodiments, the hydrophobic moieties are amino acids or amino acid analogs that have hydrophobic side chains. The amino acids or analogs are chosen to provide sufficient hydrophobicity to integrate the substrate into a micelle under the assay conditions used to detect the enzymes. Exemplary hydrophobic amino acids include alanine, glycine, valine, leucine, isoleucine, proline, phenylalanine, methionine, tryptophan, and cysteine as described in Alberts, B., et al., *Molecular Biology of the Cell*, 4$^{th}$ Ed., Garland Science, New York, N.Y., FIG. 3.3 (2002)). Exemplary amino acid analogs include norvaline, aminobutyric acid, cyclohexylalanine, butylglycine, phenylglycine, and N-methylvaline (see "Amino Acids and Amino Acid Analogs" section 2002-2003 Novabiochem catalog).

The hydrophobicity of a hydrophobic moiety can be calculated by assigning each amino acid a hydrophobicity value and then averaging the values along the hydrophobic moiety. Hydrophobicity values for the common amino acids are shown Table 2.

TABLE 2

Hydrophobicity of Amino Acids

| Amino Acid (IUPAC) | Monera et al.[1] Hydrophobicity at pH 7 | Hopp-Woods[2] Hydrophobicity scale | Kyte-Doolittle[3] Hydrophobicity scale |
|---|---|---|---|
| Alanine (A) | 41 | −0.5 | −1.8 |
| Cysteine (C) | 49 | −1.0 | −2.5 |
| Aspartic acid (D) | −55 | 3.0 | 3.5 |
| Glutamic acid (E) | −31 | 3.0 | 3.5 |
| Phenylalanine (F) | 100 | −2.5 | −2.8 |
| Glycine (G) | 0 | 0.0 | 0.4 |
| Histidine (H) | 8 | −0.5 | 3.2 |
| Isoleucine (I) | 99 | −1.8 | −4.5 |
| Lysine (K) | −23 | 3.0 | 3.9 |
| Leucine (L) | 97 | −1.8 | −3.8 |
| Methionine (M) | 74 | −1.3 | −1.9 |
| Asparagine (N) | −28 | 0.2 | 3.5 |
| Proline (P) | −46 (pH 2) | 0.0 | 1.6 |
| Glutamine (Q) | −10 | 0.2 | 3.5 |
| Arginine (R) | −14 | 3.0 | 4.5 |
| Serine (S) | −5 | 0.3 | 0.8 |
| Threonine (T) | 13 | −0.4 | 0.7 |
| Valine (V) | 76 | −1.5 | −4.2 |
| Tryptophan (W) | 97 | −3.4 | 0.9 |
| Tyrosine (Y) | 63 | −2.3 | 1.3 |

[1]Monera et al. J. Protein Sci 1: 219-329 (1995) (The values were normalized so that the most hydrophobic residue (phenylalanine) is given a value of 100 relative to glycine, which is considered neutral (0 value)).
[2]Hoop TP and Woods KR: Prediction of protein antigenic determinants from amino acid sequences. Proc Natl Acad Sci USA 78: 3824, 1981.
[3]Kyte J and Doolittle RF: A simple method for displaying the hydropathic character of a protein. J Mol Biol 157: 105, 1982.

The exact number of amino acids and/or amino acid analogs can be selectively varied as long as the hydrophobic moiety comprises sufficient hydrophobic character (e.g., length and/or size) to cause the various molecules described herein to become integrated or incorporated into a micelle when the molecules are placed in an aqueous environment at a concentration at or above its CMC. Thus, in some embodiments, the hydrophobic moiety comprises the same amino acid and/or amino acid analog. In other embodiments, the hydrophobic moiety comprises a mixture of different amino acids and/or amino acid analogs. In yet other embodiments, the hydrophobic moiety comprises a mixture of amino acids and/or amino acid analogs and hydrocarbons.

For example, if the hydrophobic moieties comprise poly (leucine) from 1 and 5 leucine residues can be used. If the hydrophobic moieties comprise poly(isoleucine) from 1 and 5 isoleucine residues can be used. If the hydrophobic moieties comprise poly(phenylalanine) from 1 and 5 phenylalanine residues can be used. If the hydrophobic moieties comprise poly(tryptophan) from 1 and 5 tryptophan residues can be used. If the hydrophobic moieties comprise a mixture of amino acids, such as leucine and isoleucine, from 1 to 5 leucine resides and from 1 to 5 isoleucine residues can be used. If the hydrophobic moieties comprise a mixture of all three amino acids, from 1 to 5 leucine residues, from 1 to 5 isoleucine residues, and from 1 to 5 phenylalanine or 1 to 5 tryptophan residues can be used. If the hydrophobic moieties comprise a mixture of four amino acids, from 1 to 5 leucine residues, from 1 to 5 isoleucine residues, from 1 to 5 phenylalanine residues and from 1 to 5 tryptophan residues can be used. In some embodiments, the hydrophobic moieties can comprise a mixture of amino acids and hydrocarbons. For example, the hydrophobic moieties can comprise from 1 to 5 residues of the amino acid leucine and from 1 to 5 hydrocarbons.

Also included herein are embodiments that involve a combination of any two or more of the foregoing embodiments.

For embodiments of substrate molecules in which the hydrophobic moieties are linked to the fluorescent moiety, it will be understood that the hydrophobic moieties are distinct from the fluorescent moiety because the hydrophobic moieties do not comprise any of the atoms in the fluorescent moiety that are part of the aromatic or conjugated pi-electron system that produces the fluorescent signal. Thus, as a specific example, if a hydrophobic moiety is connected to the C4 position of a xanthene ring (e.g., the C4' position of a fluorescein or rhodamine dye), the hydrophobic moiety does not comprise any of the aromatic ring atoms of the xanthene ring.

While the basis for increased fluorescence may not be certain, it is contemplated that the fluorescent substrates described herein are capable of forming micelles in the reaction mixture due to their hydrophobic moieties, so that the fluorescent moieties quench each other due to their close proximity and high local concentration. Micelle formation may be evidenced by an increase in light scatter and/or a shift in the absorbance maximum of the fluorescent moiety. In experiments performed in support of the compositions and methods described herein, inclusion of a single hydrophobic moiety has been found in some cases to cause a large red shift (by about 20 nm) of the absorbance maximum of the fluorescent moiety. In experiments described further below, use of two hydrophobic moieties provides a lower Km of ATP than the same sequence with a single hydrophobic moiety (see FIG. 4A-4B). Use of two hydrophobic moieties also improves the signal to background ratio under the assay conditions described herein (see FIG. 5). However, it is possible that actual formation of micelles by the substrate is not required for operability.

The fluorescent moiety in the substrate may comprise any entity that provides a fluorescent signal that can be used to follow enzyme-mediated phosphorylation. Typically, the fluorescent moiety comprises a fluorescent dye that in turn comprises a resonance-delocalized system or aromatic ring system that absorbs light at a first wavelength and emits fluorescent light at a second wavelength in response to the absorption event. A wide variety of such fluorescent dye molecules are known in the art. For example, fluorescent dyes can be selected from any of a variety of classes of fluorescent compounds, such as xanthenes, rhodamines, fluoresceins, cyanines, phthalocyanines, squaraines, and bodipy dyes.

In some embodiments, the fluorescent moiety comprises a xanthene dye. Generally, xanthene dyes are characterized by three main features: (1) a parent xanthene ring; (2) an exocyclic hydroxyl or amine substituent; and (3) an exocyclic oxo or imminium substituent. The exocyclic substituents are typically positioned at the C3 and C6 carbons of the parent xanthene ring, although "extended" xanthenes in which the parent xanthene ring comprises a benzo group fused to either or both of the C5/C6 and C3/C4 carbons are also known. In these extended xanthenes, the characteristic exocyclic substituents are positioned at the corresponding positions of the extended xanthene ring. Thus, as used herein, a "xanthene dye" generally comprises one of the following parent rings:

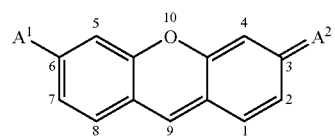

(Ia)

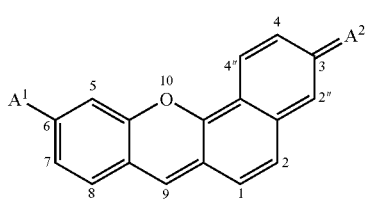

(Ib)

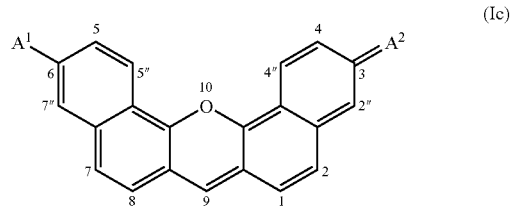

(Ic)

In the parent rings depicted above, $A^1$ is OH or $NH_2$ and $A^2$ is O or $NH_2^+$. When $A^1$ is OH and $A^2$ is O, the parent ring is a fluorescein-type xanthene ring. When $A^1$ is $NH_2$ and $A^2$ is $NH_2^+$, the parent ring is a rhodamine-type xanthene ring. When $A^1$ is $NH_2$ and $A^2$ is O, the parent ring is a rhodol-type xanthene ring.

One or both of nitrogens of $A^1$ and $A^2$ (when present) and/or one or more of the carbon atoms at positions C1, C2, C2", C4, C4", C5, C5", C7", C7 and C8 can be independently substituted with a wide variety of the same or different substituents. In some embodiments, typical substituents comprise, but are not limited to, —X, —$R^a$, —$OR^a$, —$SR^a$, —$NR^aR^a$, perhalo ($C_1$-$C_6$)alkyl, —$CX_3$, —$CF_3$, —CN, —OCN, —SCN, —NCO, —NCS, —NO, —$NO_2$, —$N_3$, —$S(O)_2O^-$, —$S(O)_2OH$, —$S(O)_2R^a$, —C(O)R, —C(O)X, —$C(S)R^a$, —C(S)X, —$C(O)OR^a$, —$C(O)O^-$, —$C(S)OR^a$, —$C(O)SR^a$, —$C(S)SR^a$, —$C(O)NR^aR^a$, —$C(S)NR^aR^a$ and —$C(NR)NR^aR^a$, where each X is independently a halogen (preferably —F or —Cl) and each $R^a$ is independently hydrogen, ($C_1$-$C_6$)alkyl, ($C_1$-$C_6$)alkanyl, ($C_1$-$C_6$)alkenyl, ($C_1$-$C_6$)alkynyl, ($C_5$-$C_{20}$)aryl, ($C_6$-$C_{26}$)arylalkyl, ($C_5$-$C_{20}$)arylaryl, 5-20 membered heteroaryl, 6-26 membered heteroarylalkyl, 5-20 membered heteroaryl-heteroaryl, carboxyl, acetyl, sulfonyl, sulfinyl, sulfone, phosphate, or phosphonate. Generally, substituents which do not tend to completely quench the fluorescence of the parent ring are preferred, but in some embodiments quenching substituents may be desirable. Substituents that tend to quench fluorescence of parent xanthene rings are electron-withdrawing groups, such as —$NO_2$, —Br and —I.

The C1 and C2 substituents and/or the C7 and C8 substituents can be taken together to form substituted or unsubstituted buta[1,3]dieno or ($C_5$-$C_{20}$) aryleno bridges. For purposes of illustration, exemplary parent xanthene rings including unsubstituted benzo bridges fused to the C1/C2 and C7/C8 carbons are illustrated below:

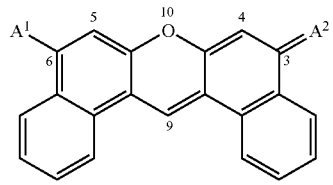

(Id)

-continued (Ie)
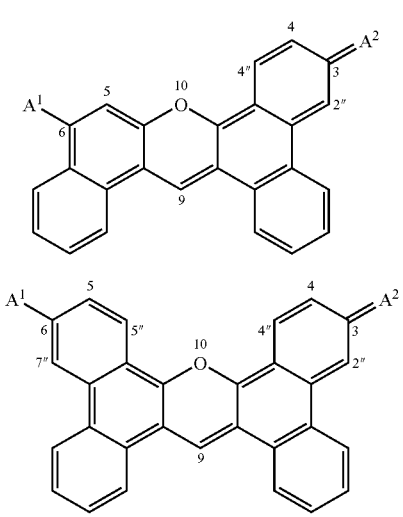

(If)
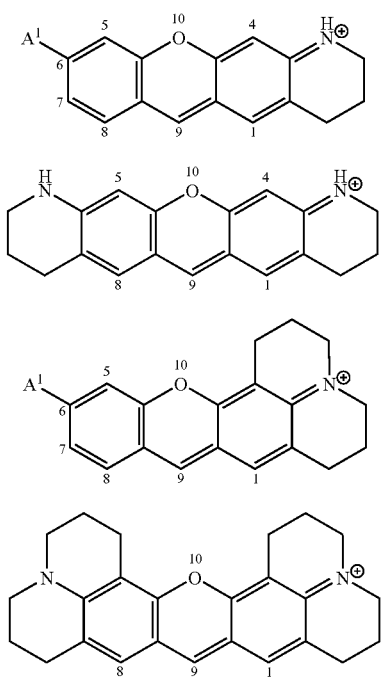

The benzo or aryleno bridges may be substituted at one or more positions with a variety of different substituent groups, such as the substituent groups previously described above for carbons C1-C8 in structures (Ia)-(Ic), supra. In embodiments including a plurality of substituents, the substituents may all be the same, or some or all of the substituents can differ from one another.

When $A^1$ is $NH_2$ and/or $A^2$ is $NH_2^+$, the nitrogen atoms may be included in one or two bridges involving adjacent carbon atom(s). The bridging groups may be the same or different, and are typically selected from $(C_1-C_{12})$alkyldiyl, $(C_1-C_{12})$alkyleno, 2-12 membered heteroalkyldiyl and/or 2-12 membered heteroalkyleno bridges. Non-limiting exemplary parent rings that comprise bridges involving the exocyclic nitrogens are illustrated below:

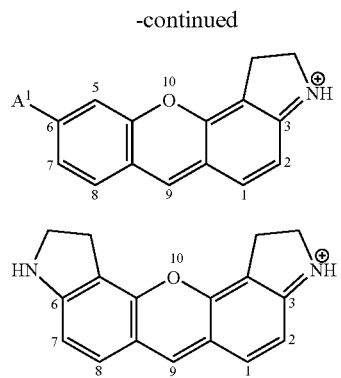

(Ig)

(Ih)

(Ii)

(Ij)

-continued (Ik)

(Il)

The parent ring may also comprise a substituent at the C9 position. In some embodiments, the C9 substituent is selected from acetylene, lower (e.g., from 1 to 6 carbon atoms)alkanyl, lower alkenyl, cyano, aryl, phenyl, heteroaryl, electron-rich heteroaryl and substituted forms of any of the preceding groups. In embodiments in which the parent ring comprises benzo or aryleno bridges fused to the C1/C2 and C7/C8 positions, such as, for example, rings (Id), (Ie) and (If) illustrated above, the C9 carbon is preferably unsubstituted.

In some embodiments, the C9 substituent is a substituted or unsubstituted phenyl ring such that the xanthene dye comprises one of the following structures:

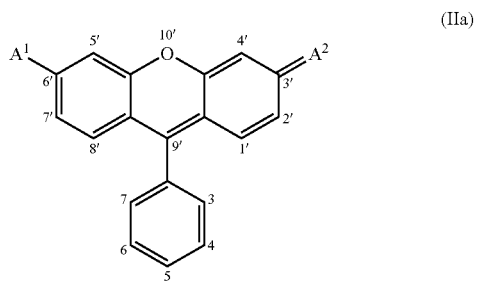

(IIa)

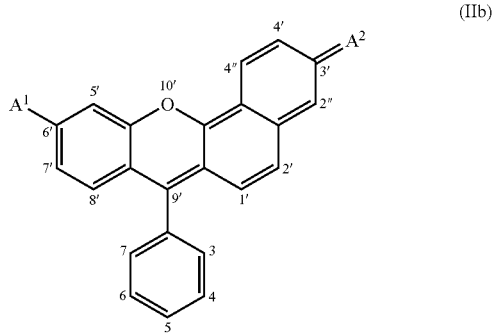

(IIb)

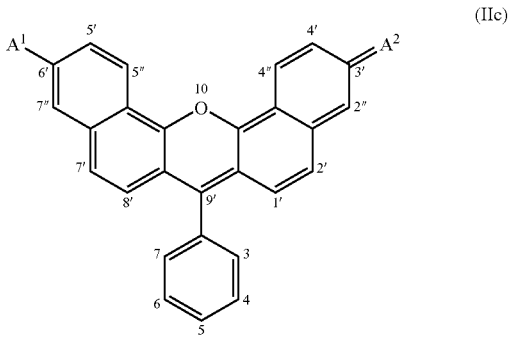

(IIc)

The carbons at positions 3, 4, 5, 6 and 7 may be substituted with a variety of different substituent groups, such as the substituent groups previously described for carbons $C_1$-$C_8$. In some embodiments, the carbon at position C3 is substituted with a carboxyl (—COOH) or sulfuric acid (—SO$_3$H) group, or an anion thereof. Dyes of formulae (IIa), (IIb) and (IIc) in which $A^1$ is OH and $A^2$ is O are referred to herein as fluorescein dyes; dyes of formulae (IIa), (IIb) and (IIc) in which $A^1$ is NH$_2$ and $A^2$ is NH$_2^+$ are referred to herein as rhodamine dyes; and dyes of formulae (Ia), (IIb) and (IIc) in which $A^1$ is OH and $A^2$ is NH$_2^+$ (or in which $A^1$ is NH$_2$ and $A^2$ is O) are referred to herein as rhodol dyes.

As highlighted by the above structures, when xanthene rings (or extended xanthene rings) are included in fluorescein, rhodamine and rhodol dyes, their carbon atoms are numbered differently. Specifically, their carbon atom numberings include primes. Although the above numbering systems for fluorescein, rhodamine and rhodol dyes are provided for convenience, it is to be understood that other numbering systems may be employed, and that they are not intended to be limiting. It is also to be understood that while one isomeric form of the dyes are illustrated, they may exist in other isomeric forms, including, by way of example and not limitation, other tautomeric forms or geometric forms. As a specific example, carboxy rhodamine and fluorescein dyes may exist in a lactone form.

In some embodiments, the fluorescent moiety comprises a rhodamine dye. Exemplary suitable rhodamine dyes include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichloro-tetramethylrhodamine (dTAMRA). Additional suitable rhodamine dyes include, for example, those described in U.S. Pat. Nos. 6,248,884, 6,111,116, 6,080,852, 6,051,719, 6,025,505, 6,017,712, 5,936,087, 5,847,162, 5,840,999, 5,750,409, 5,366,860, 5,231,191, and 5,227,487; PCT Publications WO 97/36960 and WO 99/27020; Lee et al., NUCL. ACIDS RES. 20:2471-2483 (1992), Arden-Jacob, NEUE LANWELLIGE XANTHEN-FARBSTOFFE FÜR FLUORESZENZSONDEN UND FARBSTOFF LASER, Verlag Shaker, Germany (1993), Sauer et al., J. FLUORESCENCE 5:247-261 (1995), Lee et al., NUCL. ACIDS RES. 25:2816-2822 (1997), and Rosenblum et al., NUCL. ACIDS RES. 25:4500-4504 (1997). A particularly preferred subset of rhodamine dyes are 4,7,-dichlororhodamines. In some embodiments, the fluorescent moiety comprises a 4,7-dichloro-orthocarboxyrhodamine dye.

In some embodiments, the fluorescent moiety comprises a fluorescein dye. Exemplary suitable fluorescein include, but are not limited to, fluorescein dyes described in U.S. Pat. Nos. 6,008,379, 5,840,999, 5,750,409, 5,654,442, 5,188,934, 5,066,580, 4,933,471, 4,481,136 and 4,439,356; PCT Publication WO 99/16832, and EPO Publication 050684. A preferred subset of fluorescein dyes are 4,7-dichlorofluoresceins. Other preferred fluorescein dyes include, but are not limited to, 5-carboxyfluorescein (5-FAM) and 6-carboxyfluorescein (6-FAM). In some embodiments, the fluorescein moiety comprises a 4,7-dichloro-orthocarboxyfluorescein dye.

In some embodiments, the fluorescent moiety can include a cyanine, a phthalocyanine, a squaraine, or a bodipy dye, such as those described in the following references and the references cited therein: U.S. Pat. Nos. 6,080,868, 6,005,113, 5,945,526, 5,863,753, 5,863,727, 5,800,996, and 5,436,134; and PCT Publication WO 96/04405.

In some embodiments, the fluorescent moiety can comprise a network of dyes that operate cooperatively with one another such as, for example by FRET or another mechanism, to provide large Stoke's shifts. Such dye networks typically comprise a fluorescence donor moiety and a fluorescence acceptor moiety, and may comprise additional moieties that act as both fluorescence acceptors and donors. The fluorescence donor and acceptor moieties can comprise any of the previously described dyes, provided that dyes are selected that can act cooperatively with one another. In a specific embodiment, the fluorescent moiety comprises a fluorescence donor moiety which comprises a fluorescein dye and a fluorescence acceptor moiety which comprises a fluorescein or rhodamine dye. Non-limiting examples of suitable dye pairs or networks are described in U.S. Pat. Nos. 6,399,392, 6,232,075, 5,863,727, and 5,800,996.

The kinase substrate can comprise a single fluorescent moiety or a plurality of fluorescent moieties. In embodiments employing a plurality of fluorescent moieties, the fluorescent moieties may be the same or different.

The protein kinase recognition moiety, hydrophobic moieties, and fluorescent moiety(ies) are connected in any way that permits them to perform their respective functions. In some embodiments, the protein kinase recognition moiety, the hydrophobic moieties and the fluorescent moiety(ies) can be connected directly to one another, i.e. covalently linked, to each other. In other embodiments, one or more of the protein kinase recognition moiety, the hydrophobic moieties and the fluorescent moiety(ies) can be connected indirectly to one another, i.e. via one or more optional linkers.

FIG. 1 illustrates an exemplary embodiment of a kinase substrate comprising two hydrophobic moieties, illustrated as $R^1$—C(O)— and $R^2$—C(O)—, respectively, that are attached to opposite ends of the protein kinase recognition moiety. In the illustrated hydrophobic moieties, $R^1$ and $R^2$ can comprise any of the hydrophobic groups described above. For example, in some embodiments, $R^1$ and $R^2$ can comprise saturated or unsaturated alkyl chains, which may be the same or different.

In the exemplary embodiment illustrated in FIG. 1, the first hydrophobic moiety $R_1$—C(O)— is linked to the remainder of the substrate via an optional linker 10. The presence or absence of optional linker 10 is denoted by the value for q, which may be 0 or 1. In the embodiment illustrated in FIG. 1, optional linker 10 is provided by one or more (bis)ethylene glycol group(s), also referred to herein as an "O-spacer". In the illustrated linker, the value of m can range broadly, but is typically an integer from 0 to 6. As used herein, each "O-spacer" corresponds to the bracketed illustrated structure. Thus, when m is an integer greater than one, such as, for example, three, the substrate is referred to herein as comprising three O-spacers (which can be abbreviated as "O-O-O"). As illustrated, the O-spacer comprises n oxyethylene units. As will be appreciated by a person skilled in the art, the number of oxyethylene units comprising an O-spacer can be selectively varied. For example, one, two, three or more oxyethylene units may be used to form an O-spacer. In some embodiments, n is an integer from 1 to 10. In other embodiments, n is 1, 2, 3, 4, 5 or 6.

Although exemplified with oxyethylene groups, an O-spacer need not be composed of oxyethylene units. Virtually any combination of the same or different oxyethylene units that permits the substrate to function as described herein may be used. In a specific example, an O-spacer may comprise from 1 to about 5 of the same or different lower oxyethylene units (e.g., —(CH$_2$)$_n$CH$_2$—, where x is an integer ranging from 0 to 6).

Although optional linker 10 of FIG. 1 is exemplified with an O-spacer, the chemical composition of optional linker 10 is not critical for success. The length and chemical composition of the linker can be selectively varied. In some embodiments, the linker can be selected to have specified properties. For example, the linker can be hydrophobic in character, hydrophilic in character, long or short, rigid, semirigid or flexible, depending upon the particular application. The linker can be optionally substituted with one or more substituents or one or more linking groups for the attachment of additional substituents, which may be the same or different, thereby providing a "polyvalent" linking moiety capable of conjugating or linking additional molecules or substances to the signal molecule. In certain embodiments, however, the linker does not comprise such additional substituents or linking groups.

A wide variety of linkers comprised of stable bonds that are suitable for use in the substrates described herein are known in the art, and include by way of example and not limitation, alkyldiyls, substituted alkyldiyls, alkylenos (e.g., alkanos), substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryl diyls, substituted heteroaryl-heteroaryl diyls, heteroarylalkyldiyls, substituted heteroarylalkyldiyls, heteroaryl-heteroalkyldiyls, substituted heteroaryl-heteroalkyldiyls, and the like. Thus, the linker can include single, double, triple or aromatic carbon-carbon bonds, nitrogen-nitrogen bonds, carbon-nitrogen bonds, carbon-oxygen bonds, carbon-sulfur bonds and combinations of such bonds, and may therefore include functionalities such as carbonyls, ethers, thioethers, carboxamides, sulfonamides, ureas, urethanes, hydrazines, etc. In some embodiments, the linker comprises from 1-20 non-hydrogen atoms selected from the group consisting of C, N, O, and S and is composed of any combination of ether, thioether, amine, ester, carboxamide, sulfonamides, hydrazide, aromatic and heteroaromatic groups.

Choosing a linker having properties suitable for a particular application is within the capabilities of those having skill in the art. For example, where a rigid linker is desired, it may comprise a rigid polypeptide such as polyproline, a rigid polyunsaturated alkyldiyl or an aryldiyl, biaryldiyl, arylaryldiyl, arylalkyldiyl, heteroaryldiyl, biheteroaryldiyl, heteroarylalkyldiyl, heteroaryl-heteroaryldiyl, etc. Where a flexible linker is desired, it may comprise a flexible polypeptide such as polyglycine or a flexible saturated alkanyldiyl or heteroalkanyldiyl. Hydrophilic linkers may comprise, for example, polyalcohols or polyethers such as polyalkyleneglycols, and O-spacers, as described above. Hydrophobic linkers may comprise, for example, alkyldiyls or aryldiyls.

In the exemplary kinase substrate of FIG. 1, the linkage linking the first hydrophobic moiety to the illustrated linker 10 (as well as the linkages linking the other moieties and optional linkers to one another) is a peptide bond. Skilled artisans will appreciate that while using peptide bonds may be convenient, the various moieties comprising the substrates can be linked to one another via any linkage that is stable to the conditions under which the substrates will be used. In some embodiments, the linkages are formed from pairs of complementary reactive groups capable of forming covalent linkages with one another. "Complementary" nucleophilic and electrophilic groups (or precursors thereof that can be suitable activated) useful for effecting linkages stable to biological and other assay conditions are well known. Examples of suitable complementary nucleophilic and electrophilic groups, as well as the resultant linkages formed therefrom, are provided in Table 3.

TABLE 3

| Electrophilic Group | Nucleophilic Group | Resultant Covalent Linkage |
|---|---|---|
| activated esters* | Amines/anilines | carboxamides |
| Acyl azides** | Amines/anilines | carboxamides |
| Acyl halides | Amines/anilines | carboxamides |
| Acyl halides | alcohols/phenols | esters |
| Acyl nitriles | alcohols/phenols | esters |
| Acyl nitriles | Amines/anilines | carboxamides |
| aldehydes | Amines/anilines | imines |
| aldehydes or ketones | Hydrazines | hydrazones |
| aldehydes or ketones | Hydroxylamines | oximes |
| Alkyl halides | Amines/anilines | alkyl amines |
| Alkyl halides | carboxylic acids | esters |
| Alkyl halides | Thiols | thioethers |
| Alkyl halides | alcohols/phenols | ethers |
| Alkyl sulfonates | Thiols | thioethers |
| Alkyl sulfonates | carboxylic acids | esters |
| Alkyl sulfonates | alcohols/phenols | esters |
| anhydrides | alcohols/phenols | esters |
| anhydrides | Amines/anilines | caroboxamides |
| Aryl halides | Thiols | thiophenols |
| Aryl halides | Amines | aryl amines |
| aziridines | Thiols | thioethers |
| boronates | Glycols | boronate esters |
| carboxylic acids | Amines/anilines | carboxamides |
| carboxylic acids | Alcohols | esters |
| carboxylic acids | Hydrazines | hydrazides |
| carbodiimides | carboxylic acids | N-acylureas or anhydrides |
| diazoalkanes | carboxylic acids | esters |
| epoxides | Thiols | thioethers |
| haloacetamides | Thiols | thioethers |
| halotriazines | Amines/anilines | aminotriazines |
| halotriazines | alcohols/phenols | triazinyl ethers |
| Imido esters | Amines/anilines | amidines |
| isocyanates | Amines/anilines | ureas |
| isocyanates | alcohols/phenols | urethanes |
| isothiocyanates | Amines/anilines | thioureas |
| maleimides | Thiols | thioethers |
| phosphoramidites | Alcohols | phosphate esters |
| Silyl halides | Alcohols | silyl ethers |
| sulfonate esters | Amines/anilines | alkyl amines |
| sulfonate esters | Thiols | thioethers |
| sulfonate esters | carboxylic acids | esters |
| sulfonate esters | Alcohols | esters |
| sulfonyl halides | Amines/anilines | sulfonamides |
| sulfonyl halides | phenols/alcohols | sulfonate esters |

*Activated esters, as understood in the art, generally have the formula —C(O)Z, where Z is, a good leaving group (e.g., oxysuccinimidyl, oxysulfosuccinimidyl, 1-oxybenzotriazolyl, etc.).
**Acyl azides can rearrange to isocyanates.

In the exemplary embodiment illustrated in FIG. 1, the fluorescent moiety (Dye-C(O)— is linked to the first hydrophobic moiety and the N-terminal end of the protein recognition moiety via a multivalent (trivalent) linker, which in the specific embodiment illustrated in FIG. 1 is provided by the amino acid lysine. As will be appreciated by a person of skill in the art, the illustrated lysine is merely an exemplary trivalent linker. Any molecule having three or more "reactive" groups suitable for attaching other molecule and moieties thereto, or that can be appropriately activated to attach other molecules and moieties thereto could be used to provide a trivalent or higher order multivalent linker. For example, the "backbone" of the multivalent linker to which the reactive linking groups are attached could be linear, branched or cyclic saturated or unsaturated alkyl, a mono or polycyclic aryl or an arylalkyl. Moreover, while the previous examples are hydrocarbons, the multivalent linker backbone need not be limited to carbon and hydrogen atoms. Thus, a multivalent linker backbone can include single, double, triple or aromatic carbon-carbon bonds, carbon-nitrogen bonds, nitrogen-nitrogen bonds, carbon-oxygen bonds, carbon-sulfur bonds and combinations thereof, and therefore can include functionalities such as carbonyls, ethers, thioethers, carboxamides, sulfonamides, ureas, urethanes, hydrazines, etc.

In the specific embodiment illustrated in FIG. 1, the protein kinase recognition moiety comprises the peptide sequence RRIPSP. It will appreciated that this sequence is for purposes of illustration only, and that virtually any protein kinase sequence, such as the various exemplary sequences provided in Table 1, supra, may be used. Skilled artisans will be readily able to select a protein kinase recognition sequence suitable for a particular application.

The second hydrophobic moiety, represented by $R^2$—C(O)—, is linked the C-terminal end of the protein kinase recognition moiety. As illustrated, the linkage, which is effected through the use of a multivalent lysine residue, is spaced away from the C-terminus of the protein recognition sequence via optional linker 12. Optional linker 12 is similar in concept and function to optional linker 10. Although it is illustrated as being composed of O-spacer, like optional linker 10, it need not be. Optional linker 12 can comprise an of the various atoms and groups discussed above in connection with optional linker 10. When as illustrate in FIG. 1, both optional linkers are present (each q=1) and composed of O-spacers. The number of O-spacers comprising each linker can be selectively varied resulting in O-linkers of different lengths.

Optional linkers 10 and 12 may both be present, they may both be absent, or, alternatively, one of linkers 10 and 12 may be present and the other absent. For example, an optional linker 10 can be used to connect the first hydrophobic moiety to the N-terminal end of the protein kinase recognition moiety, while the second hydrophobic moiety can be linked to the C-terminal end of the protein kinase recognition moiety with the aid of optional linker 12.

Moreover, while the second hydrophobic moiety of the exemplary kinase substrate of FIG. 1 is linked to optional linker 12 via a trivalent lysine linker, it could be linked directly to the end of linker 12 (see, e.g., FIG. 2A) or directly to the C-terminus of the protein recognition moiety without the aid of any linkers.

Although the various hydrophobic, fluorescent, protein kinase recognition and optional linker moieties comprising the exemplary kinase substrate of FIG. 1 are linked in a specified configuration, other configurations are possible. Additional exemplary embodiments of kinase substrates are illustrated in FIG. 2. In FIGS. 2A-2E, each illustrated $R^1$, $R^2$, Dye, n, m and q is, independently of any others that may be illustrated, as defined for FIG. 1. Each illustrated p is, independently of the others, an integer ranging from about 1 to about 6.

FIG. 2A illustrates an exemplary kinase substrate that is similar to the exemplary kinase substrate of FIG. 1, with the exception that the second hydrophobic moiety, represented by $R^2$—NH—, is linked directly to the optional linker. FIG. 2B illustrates an exemplary embodiment of a kinase substrate that comprises two fluorescent moieties. Although the two fluorescent moieties are illustrated as being the same, they could be different. FIG. 2C illustrates an exemplary kinase that is similar to the exemplary kinase substrate of FIG. 2B, with the exception that the second hydrophobic moiety, represented by $R^2$—NH—, is linked directly to the optional linker. FIG. 2D illustrates an exemplary kinase substrate that is similar to the exemplary kinase substrate of FIG. 1, with the exception that the fluorescent moiety is linked to the C-terminal end of the protein kinase recognition moiety via an optional linker. FIG. 2E illustrates an exemplary embodiment of a kinase substrate that is similar to the kinase substrate of FIG. 2A, with the exception that the optional linker intervenes the fluorescent moiety and the protein kinase recognition moiety instead of the first hydrophobic moiety and the fluorescent moiety.

Skilled artisans will appreciate that while the kinase substrates illustrated in FIGS. 2A-2E are exemplified with specific hydrophobic moieties, fluorescent moieties, protein kinase recognition sequences and optional linkers, any one or more of these features of the illustrated kinase substrates could be varied. As a specific example, while the substrates are exemplified with optional O-linkers (described above), in embodiments employing one or more linkers, any linker could be used, as described above. Moreover, while the various moieties are illustrated as being linked with amide linkages, virtually any type of chemical linkage(s) that are stable to the assay conditions and that permit the various moieties to perform their respective functions could be used. Additionally, the various illustrated features can be readily "mixed and matched" to provide other specific embodiments of exemplary kinase substrates.

An exemplary kinase substrate, $R_1$-OO-K(Dye2)-RRIPLSP-OO-K($R^2$)-NH$_2$ is illustrated in FIG. 3 (SEQ ID NO: 20).

In some embodiments, the substrate compounds described herein are not cleavable by phospholipases.

The substrate may be designed to have a particular net charge in the unphosphorylated state. In some embodiments, the substrate has a net charge of 0 (a net neutral charge), or about 0, when measured at pH 7.6, such that addition of a phosphate group yields a product having a net charge of negative 2. In other embodiments, the substrate has a net charge that is different from 0, such as −1, −2, or +1. In some embodiments, the net charge of the substrate is 0 or less. In other embodiments, the net charge is −1 or less. By increasing the amplitude of the net negative charge of the substrate by −2 due to phosphorylation, a phosphorylated product is formed that is less stable in micellar form than the substrate. Accordingly, the product is more fluorescent that the substrate, so that enzyme activity can be readily detected.

The net charge of the substrate can be established by including an appropriate number of negatively and positively charged groups in the substrate. For example, to establish a net neutral charge (net charge=0), the substrate is designed to contain an equal number of positively and negatively charged groups. Lysine and arginine contain side chains that carry a single positive charge at physiological pH (pH=6 to 8). Aspartate and glutamate contain carboxyl side chains having a single negative charge. A phosphoserine residue carries two negative charges on a phosphate group. The imidazole side chain of histidine has a pK of about 7, so it carries a full positive charge at a pH of about 6 or less. Cysteine has a pK of about 8, so it carries a full negative charge at a pH of about 9 or higher. In addition, the fluorescent moiety may also contain charged groups that should be considered to obtain a particular net charge of the substrate.

The substrates can be readily formed by synthetic methods known in the art. Polypeptides can be prepared by automated synthesizers on a solid support (Perkin *J. Am. Chem. Soc.* 85:2149-2154 (1963)) by any of the known methods, e.g. Fmoc or BOC (e.g., Atherton, *J. Chem. Soc.*

538-546 (1981); *Fmoc Solid Phase Peptide Synthesis. A Practical Approach*, Chan, Weng C. and White, Peter D., eds., Oxford University Press, New York, 2000). Synthetically, polypeptides may be formed by a condensation reaction between the α-carbon carboxyl group of one amino acid and the amino group of another amino acid. Activated amino acids are coupled onto a growing chain of amino acids, with appropriate coupling reagents. Polypeptides can be synthesized with amino acid monomer units where the α-amino group was protected with Fmoc (fluorenylmethoxycarbonyl). Alternatively, the BOC method of peptide synthesis can be practiced to prepare the peptide conjugates described herein.

Amino acids with reactive side-chains can be further protected with appropriate protecting groups. Amino groups on lysine side-chains to be labelled can be protected with an Mtt protecting group, selectively removable with about 5% trifluoroacetic acid in dichloromethane. A large number of different protecting group strategies can be employed to efficiently prepare polypeptides.

Exemplary solid supports include polyethyleneoxy/polystyrene graft copolymer supports (TentaGel, Rapp Polymere GmbH, Tubingen, Germany) and a low-cross link, high-swelling Merrifield-type polystyrene supports with an acid-cleavable linker (Applied Biosystems), although others can be used as well.

Polypeptides are typically synthesized on commercially available synthesizers at scales ranging from 3 to 50 µmoles. The Fmoc group is removed from the terminus of the peptide chain with a solution of piperidine in dimethylformamide (DMF), typically 30% piperidine, requiring several minutes for deprotection to be completed. The amino acid monomer, coupling agent, and activator are delivered into the synthesis chamber or column, with agitation by vortexing or shaking. Typically, the coupling agent is HBTU, and the activator is 1-hydroxybenzotriazole (HOBt). The coupling solution also may contain diisopropylethylamine or another organic base, to adjust the pH to an optimal level for rapid and efficient coupling.

Peptides may alternatively be prepared on chlorotrityl polystyrene resin by typical solid-phase peptide synthesis methods with a Model 433A Peptide Synthesizer (Applied Biosystems, Foster City, Calif.) and Fmoc/HBTU chemistry (Fields, (1990) Int. J. Peptide Protein Res. 35:161-214). The crude protected peptide on resin may be cleaved with 1% trifluoroacetic acid (TFA) in methylene chloride for about 10 minutes. The filtrate is immediately raised to pH 7.6 with an organic amine base, e.g. 4-dimethylaminopyridine. After evaporating the volatile reagents, a crude protected peptide is obtained that can be labelled with additional groups.

Following synthesis, the peptide on the solid support (resin) is deprotected and cleaved from the support. Deprotection and cleavage may be performed in any order, depending on the protecting groups, the linkage between the peptide and the support, and the labelling strategy. After cleavage and deprotection, peptides may be desalted by gel filtration, precipitation, or other means, and analyzed. Typical analytical methods useful for the peptides and peptide conjugates described herein include mass spectroscopy, absorption spectroscopy, HPLC, and Edman degradation sequencing. The peptides and peptide conjugates described herein may be purified by reverse-phase HPLC, gel filtration, electrophoresis, or dialysis.

Polypeptides may be conjugated, or "labelled," with a fluorescent dye to provide the fluorescent moiety in the substrate. Typically, a fluorescent dye labelling reagent bears an electrophilic linking moiety which reacts with a nucleophilic group on the polypeptide, e.g. amino terminus, or side-chain nucleophile of an amino acid. Alternatively, the dye may have a nucleophilic moiety, e.g. amino- or thiol-linking moiety, which reacts with an electrophilic group on the peptide, e.g. NHS of the carboxyl terminus or carboxyl side-chain of an amino acid. The polypeptide may be on a solid support, i.e. synthesis resin, during the labelling reaction. Alternatively, the polypeptide may have been cleaved prior to labelling.

Methods for modifying proteins by labeling with reporter molecules, such as fluorescent dyes, are well know in the art. (e.g. Means, G. E. and Feeney, R. E. (1971) Chemical Modification of Proteins, Holden-Day, San Francisco, Calif.; Means (1990) Bioconjugate Chem. 1:2; Glazer et al. (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) Chemical Modification of Proteins, In Modern Methods in Protein Chemistry, H. Tschesche, Ed., Walter DeGryter, Berlin and New York; Wong (1991) Chemistry of Protein Conjugation and Cross-linking, CRC Press, Boca Raton, Fla.).

Fluorescent dyes that can be used to prepare the kinase substrate molecule can be prepared synthetically using conventional methods or purchased commercially (e.g. Sigma-Aldrich and/or Molecular Probes). Non-limiting examples of methods that can be used to synthesize suitably reactive fluorescein and/or rhodamine dyes can be found in the various patents and publications discussed above in connection with the fluorescent moiety. Non-limiting examples of suitably reactive fluorescent dyes that are commercially available from Molecular Probes (Eugene, Oreg.) are provided in Table 4, below:

TABLE 4

| Catalog Number | Product Name |
| --- | --- |
| C-20050 | 5-carboxyfluorescein-bis-(5-carboxymethoxy-2-nitrobenzyl) ether, -alanine-carboxamide, succinimidyl ester (CMNB-caged carboxyfluorescein, SE) |
| C-2210 | 5-carboxyfluorescein, succinimidyl ester (5-FAM, SE) |
| C-1311 | 5-(and-6)-carboxyfluorescein, succinimidyl ester (5(6)-FAM, SE) |
| D-16 | 5-(4,6-dichlorotriazinyl) aminofluorescein (5-DTAF) |
| F-6106 | 6-(fluorescein-5-carboxamido)hexanoic acid, succinimidyl ester (5-SFX) |
| F-2182 | 6-(fluorescein-5-(and-6)-carboxamido) hexanoic acid, succinimidyl ester (5(6)-SFX) |

TABLE 4-continued

| Catalog Number | Product Name |
| --- | --- |
| F-6129 | 6-(fluorescein-5-(and-6)-carboxamido) hexanoic acid, succinimidyl ester (5(6)-SFX) |
| F-6130 | fluorescein-5-EX, succinimidyl ester |
| F-143 | fluorescein-5-isothiocyanate (FITC 'Isomer I') |
| F-1906 | fluorescein-5-isothiocyanate (FITC 'Isomer I') |
| F-1907 | fluorescein-5-isothiocyanate (FITC 'Isomer I') |
| F-144 | fluorescein-6-isothiocyanate (FITC 'Isomer II') |
| T-353 | TEXAS RED ® sulfonyl chloride |

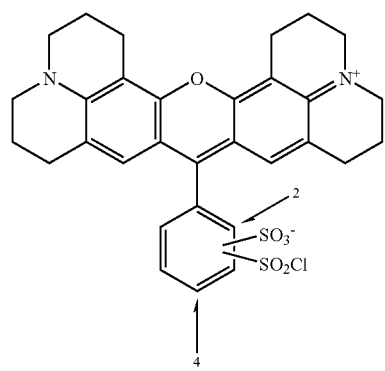

T-1905   TEXAS RED ® sulfonyl chloride

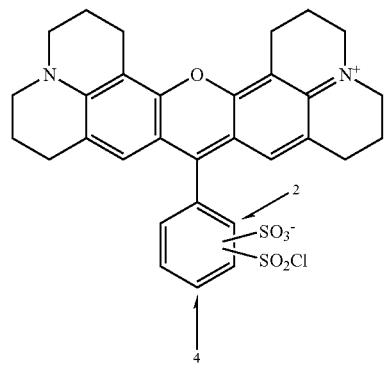

T-10125   TEXAS RED ®-X_STP ester, sodium salt

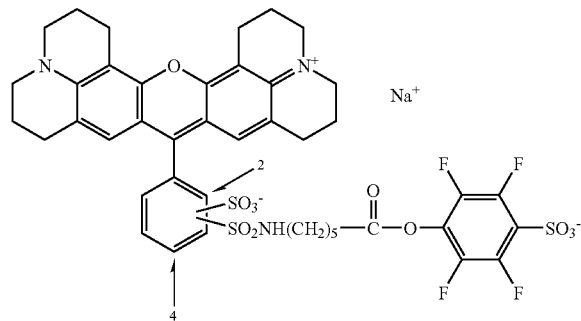

TABLE 4-continued

| Catalog Number | Product Name |
|---|---|
| T-6134 | TEXAS RED ®-X, succinimidyl ester 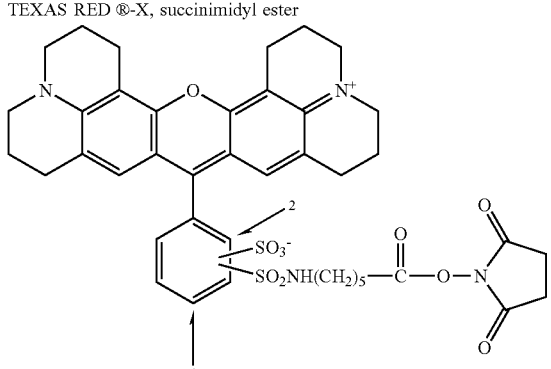 |
| T-20175 | TEXAS RED ®-X, succinimidyl ester 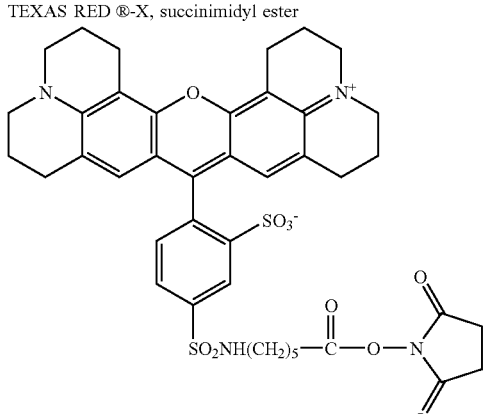 |

Polypeptides may contain a number of reactive amino acid side chains. Certain amino acid side-chains allow labelling with activated forms of fluorescent dye labelling reagents. Aspartic acid, glutamic acid, lysine, arginine, cysteine, histidine, tyrosine, and other amino acids have reactive functionality for labelling. By appropriate selection of protecting groups, certain reactive functionality on the peptide can be selectively unmasked for reaction with a labelling reagent. Specific reactive moieties can be introduced into the polypeptide by chemical modification of reactive side chains. The reactive side chains may be naturally a part of the protein or are artificially introduced during peptide synthesis or by post-synthesis modification, e.g. by deprotection (Coull, U.S. Pat. No. 6,197,513). They serve as "handles" for attaching a wide variety of molecules, including labels or other proteins. Amines (lysines, α-amino Groups) are the most common reactive groups of proteins, e.g. the aliphatic ∈-amine of the amino acid lysine. Lysines are usually present to some extent and are often quite abundant. Lysine amines ($pK_a$=9.2) are reasonably good nucleophiles under neutral or basic conditions, e.g. above pH 8.0 (Fasman, G. D. Ed. (1989) Practical Handbook of Biochemistry and Molecular Biology, p13, CRC Press, Boca Raton, Fla.) and therefore react with a variety of reagents to form stable bonds (eq 1).

Protein-$NH_2$+RX→Protein-NHR+XH      (1)

Other reactive amines that are found in proteins are the α-amino groups of the N-terminal amino acids that are less basic than lysines and are reactive at around pH 7. Sometimes they can be selectively modified in the presence of lysines. There is usually at least one α-amino acid in a protein, and in the case of proteins that have multiple peptide chains or several subunits, there can be more (one for each peptide chain or subunit).

Thiols (sulfhydryls, mercaptans) are another reactive group in the cystine, cysteine, methionine side chains. Cysteine contains a free thiol group, which is more nucleophilic than amines and is generally the most reactive functional group in a protein. It reacts with some of the same modification reagents as do the amines discussed in the previous section and in addition can react with reagents that are not very reactive toward amines. Thiols are reactive at neutral pH, and may be coupled to other molecules selectively in the presence of amines under certain conditions (eq 2).

$NH_2$-Protein-SH+RX→$NH_2$-Protein-SR+XH      (2)

Since free thiol groups are relatively reactive, proteins with thiols often exist in their oxidized form as disulfide-linked oligomers or have internally bridged disulfide groups. Reduction of the disulfide bonds with a reagent such as dithiothreitol (DTT) is required to generate the reactive free thiol. In addition to cystine and cysteine, some proteins also have the amino acid methionine, which contains sulfur in a methylthioether form.

Amine-reactive labelling reagents may react with lysines and the α-amino groups of proteins and peptides under both aqueous and nonaqueous conditions. Reactive esters, especially N-hydroxysuccinimide (NHS) esters, are among the most commonly used amine-reactive reagents for modification of polypeptide amine groups. These reagents have high selectivity toward aliphatic amines. Their reaction rates with aromatic amines, alcohols (serine, threonine), phenols (tyrosine), and histidine are relatively low. The aliphatic amide products which are formed are very stable. NHS esters are commercially available with sulfonate groups, with increased water solubility (see Brinkley, 1992, *Bioconjugate Chem.* 3:2).

Of the many reactions that may be performed at protein amino groups, one useful for labelling purposes is acylation, or reactions that may be considered analogous to acylation. Acylation reactions may be described by the following general scheme:

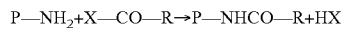

where P is the protein, X is a leaving group and R is the function being introduced, e.g. a fluorescent dye. The active reagent X—CO—R may be produced in situ by the action of an activating agent, such as a carbodiimide, on the free carboxylic acid of the label reagent. Alternatively, stable active esters may be stored as solid reagents. Other amine-reactive labelling reagents, X—CO—R, have electrophilic functional groups such as: isothiocyanate (e.g. FITC, fluorescein isothiocyanate), sulphonyl halide and dichlorotriazine. Thiol-reactive labelling reagents include iodoacetyl and maleimido derivatives. Iodoacetyl and maleimido reagents may be used for amine modification also, but a higher pH (>9.0) and longer reaction times are required.

The fluorescent dye label reagents include a reactive linking group, "linking moiety," at one of the substituent positions for covalent attachment of the dye to a polypeptide. Linking moieties capable of forming a covalent bond are typically electrophilic functional groups capable of reacting with nucleophilic molecules, such as alcohols, alkoxides, amines, hydroxylamines, and thiols. Examples of electrophilic linking moieties include succinimidyl ester, isothiocyanate, sulfonyl chloride, sulfonate ester, silyl halide, 2,6-dichlorotriazinyl, pentafluorophenyl ester, phosphoramidite, maleimide, iodoacetamide, haloacetyl, epoxide, alkylhalide, allyl halide, aldehyde, ketone, acylazide, and anhydride.

The ester N-hydroxysuccinimide (NHS) and the more water-soluble sulphonated form (NHSS), are efficient due to their stability as reagents, convenient reaction times due to their reactivity with protein amino groups (typically 0.5-2 h), and relative ease of synthesis. The NHS ester form of the dye is exemplified by the structure:

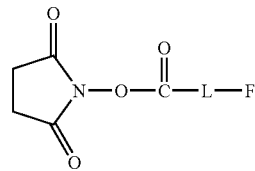

where F is the fluorescent moiety. The linkage L may be a bond or an uncharged linker such as $C_1$-$C_{30}$ alkyldiyl, an oxo-alkyl, a terpene, a lipid, a fatty acid, or a steroid. The linker can have functional groups including —C(O)—, —C(O)O—, —O—, —S—, —S—S—, —C(O)NR—, —OC(O)NR, —NRC(O)NR, and —NRC(S)NR; where R is selected from H, $C_1$-$C_6$ alkyl and $C_5$-$C_{14}$ aryl.

The activated ester, e.g. NHS or HOBt, of the dye may be preformed, isolated, purified, and/or characterized, or it may be formed in situ and reacted with a nucleophilic group of a polypeptide. Typically, a carboxyl substituent of a fluorescent dye is activated by reacting with some combination of: (1) a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N, N',N'-tetramethyluronium hexafluorophosphate), or HATU (O-(7-azabenzotriazol-1-yl)-N,N,N',N'-tetramethyluronium hexafluorophosphate); (2) an activator, such as 1-hydroxybenzotriazole (HOBt) or 1-hydroxyazabenotriazole (HOAt); and (3) N-hydroxysuccinimide to give the NHS ester of the dye.

Other activating and coupling reagents include TBTU (2-(1H-benzotriazo-1-yl)-1-1,3,3-tetramethyluronium hexafluorophosphate), TFFH(N,N',N",N'"-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and arylsulfonyl halides, e.g. triisopropylbenzenesulfonyl chloride.

One synthetic route to fluorescent dye labelled polypeptides entails conjugating a fluorescent dye reagent to the N-terminus of a resin-bound peptide before removal of other protecting groups and release of the labeled peptide from the resin. About five equivalents of an amine-reactive fluorophore are usually used per amine of the immobilized peptide. Xanthene fluorophores, including fluoresceins and rhodols are reasonably stable to hydrogen fluoride (HF), as well as to most other acids, after the BOC method of synthesis. These fluorophores are also stable to reagents used for deprotection of peptides synthesized using FMOC chemistry. (Haugland, 1996, Molecular Probes Handbook of Fluorescent Probes and Research Chemicals, Molecular Probes, Inc, Eugene Oreg.).

In another aspect, a method for detecting the phosphatase activity of one or more protein phosphatases in a sample is provided. In the method, a mixture is provided comprising a sample and a phosphatase substrate, wherein the phosphatase substrate comprises (a) a phosphatase recognition moiety containing at least one phosphorylated residue that is capable of being dephosphorylated (hydrolyzed) by a phosphatase, (b) two or more hydrophobic moieties capable of integrating the substrate into a micelle, and (c) a fluorescent moiety. The mixture is subjected to conditions effective to allow dephosphorylation of the phosphorylated residue when a phosphatase is present in the sample, thereby increasing a fluorescent signal produced by the fluorescent moiety. Detection of an increase in fluorescent signal in the mixture indicates the presence of a phosphatase in the sample.

The phosphatase to be detected can be any phosphatase known in the art. Also, the phosphatase can be a phosphatase candidate, and the method is used to confirm and/or characterize the kinase activity of the candidate.

A wide variety of protein phosphatases have been identified (e.g., see P. Cohen, *Ann. Rev. Biochem.* 58:453-508 (1989), *Molecular Biology of the Cell*, 3rd edition, Alberts et al., eds., Garland Publishing, NY (1994), and *Chem. Rev.* 101:2209-2600, "Protein Phosphorylation and Signaling" (2001)). Serine/threonine protein phosphatases represent a large class of enzymes that reverse the action of protein kinase A enzymes, for example. The serine/threonine protein phosphatases have been divided among four groups designated I, IIA, IIB, and IIC. Protein tyrosine kinases are also an important class of phosphatases, and histidine, lysine, arginine, and aspartate phosphatases are also known (e.g., see P. J. Kennelly, *Chem Rev.* 101:2304-2305 (2001) and references cited therein). In some cases, phosphatases are highly specific for only one or a few proteins, but in other cases, phosphatases are relatively non-specific and can act on a large range of protein targets. Accordingly, the phosphatase substrates described herein can be designed to detect particular phosphatases by suitable selection of the phosphatase recognition moiety. Examples of peptide sequences that can be dephosphorylated by phosphatase activity are described in P. J. Kennelly, *Chem. Rev.* 101:2291-2312 (2001).

The phosphatase substrate can be designed to be reactive with a particular phosphatase or a group of phosphatases, or it can be designed to determine substrate specificity and other catalytic features, such as determining a value for kcat or Km. The phosphorylated residue in the phosphatase recognition moiety may be any group that is capable of being dephosphorylated by a phosphatase. In some embodiments, the residue is a phosphotyrosine residue. In other embodiments, the residue is a phosphoserine residue. In yet other embodiments, the residue is a phosphothreonine residue.

In addition to having one or more phosphorylated residues capable of being dephosphorylated, the recognition moiety may include additional amino acid residues (or analogs thereof) that facilitate binding specificity, affinity, and/or rate of dephosphorylation by the phosphatase.

The recognition moiety may comprise a polypeptide segment containing the group or residue that is to be dephosphorylated. In some embodiments, the polypeptide segment has a polypeptide length equal to or less than 30 amino acid residues, 25 residues, 20 residues, 15 residues, 10 residues, or 5 residues. In other embodiments, the polypeptide segment has a polypeptide length in a range of 3 to 30 residues, or 3 to 25 residues, or 3 to 20 residues, or 3 to 15 residues, or 3 to 10 residues, or 3 to 5 residues, or 5 to 30 residues, or 5 to 25 residues, or 5 to 20 residues, or 5 to 15 residues, or 5 to 10 residues, or 10 to 30 residues, or 10 to 25 residues, or 10 to 20 residues, or 10 to 15 residues. In other embodiments, the polypeptide segment contains 3 to 30 amino acid residues, or 3 to 25 residues, or 3 to 20 residues, or 3 to 15 residues, or 3 to 10 residues, or 3 to 5 residues, or 5 to 30 residues, or 5 to 25 residues, or 5 to 20 residues, or 5 to 15 residues, or 5 to 10 residues, or 10 to 30 residues, or 10 to 25 residues, or 10 to 20 residues, or 10 to 15 residues. In other embodiments, the polypeptide segment contains at least 3, 4, 5, 6 or 7 amino acid residues.

The hydrophobic moieties in the substrate, either individually or together, are capable of integrating the substrate into a micelle. The hydrophobic moieties may have the same features as described above with respect to the hydrophobic moieties for the protein kinase substrates above. The hydrophobic moieties are preferably chosen to facilitate an increase in fluorescence of the fluorescent moiety upon dephosphorylation of the substrate, such that the amplitude of the increase is greater than would be obtained with the same substrate structure lacking the hydrophobic moiety, or with the same substrate structure comprising a single hydrophobic moiety.

The substrate may be designed to have a particular net charge in the phosphorylated state. In some embodiments, the substrate has a net charge of 0 (a net neutral charge), or about 0, when measured at pH 7.6, such that removal of a phosphate group yields a product having a net charge of +2. In other embodiments, the substrate has a net charge that is different from 0, such as +1, +2, or −1. In other embodiments, the net charge of the substrate is 0 or greater. In yet other embodiments, the net charge is +1 or greater.

The fluorescent moiety of the phosphatase substrate may be any fluorescent entity that is operative in accordance with the present teachings. In some embodiments, the fluorescent moiety comprises a fluorescein. In other embodiments, the fluorescent moiety comprises a sulfofluorescein. In yet other embodiments, the fluorescent moiety comprises a rhodamine. Other fluorescent moieties may also be used, of the same type discussed above with respect to protein kinase substrates.

The phosphatase recognition moiety, hydrophobic moieties, and fluorescent moiety are connected in any way that permits them to perform their respective functions, in a manner analogous to the design considerations discussed herein with respect to protein kinase substrates.

More generally, substrates for detecting an enzyme, such as a protein kinase, phosphatase, or other enzyme, may be designed to have any of the following features, including any combinations thereof. In some embodiments, the fluorescence of the product of the enzyme reaction is at least 2 times, at least 3 times, at least 4 times, or at least 5 times the fluorescence of the substrate, on a mole:mole basis. In other embodiments, the substrate has a molecular weight of less than 5000 daltons, or less than 4000 daltons, or less than 3000 daltons, or less than 2000 daltons. In still other embodiments, the substrate excludes (does not comprise) structures in which the fluorescent moiety is bound to an apoenzyme or apoprotein.

III. Methods

The sample to be tested may be any suitable sample selected by the user. The sample may be naturally occurring or man-made. For example, the sample may be a blood sample, tissue sample, cell sample, buccal sample, skin sample, urine sample, water sample, or soil sample. The sample can be from a living organism, such as a eukaryote, prokaryote, mammal, human, yeast, or bacterium. The sample may be processed prior to contact with a substrate described herein by any method known in the art. For example, the sample may be subjected to a precipitation step, column chromatography step, heat step, etc. In some cases, the sample is a purified or synthetically prepared enzyme that is used to screen for or characterize an enzyme substrate, inhibitor, activator, or modulator.

If the sample contains both a kinase and a phosphatase, so that the activity of one may interfere with the activity of the other, then an inactivating agent (e.g., an active site directed an irreversible inhibitor) can be added to the sample to inactivate whichever activity is not desired.

The reaction mixture typically includes a buffer, such as a buffer described in the "Biological Buffers" section of the 2000-2001 Sigma Catalog. Exemplary buffers include MES, MOPS, HEPES, Tris (Trizma), bicine, TAPS, CAPS, and the like. The buffer is present in an amount sufficient to generate and maintain a desired pH. The pH of the reaction mixture is selected according to the pH dependency of the activity of the enzyme to be detected. For example, the pH can be from 2 to 12, from 4 to 11, or from 6 to 10. The reaction mixture also contains any necessary cofactors and/or cosubstrates for the enzyme (e.g., ATP for a protein kinase, $Ca^{2+}$ ion for a calcium dependent kinase, and cAMP for a protein kinase A). Additional mixture components are discussed in Section IV below. In some embodiments, the reaction mixture does not contain detergent or is substantially free from detergents.

In some embodiments, it may be desirable to keep the ionic strength as low as reasonably possible to help avoid masking charged groups in the reaction product, so that micelle formation of product molecules remains disfavored and destabilized. For example, high salt concentration (e.g., 1 M NaCl) may be inappropriate. In addition, it may be desirable to avoid high concentrations of certain other components in the reaction mixture that can also adversely affect the fluorescence properties of the product. Guidance regarding the effects of ionic species, such as metal ions, can be found in *Surfactants and Interfacial Phenomena*, 2nd Ed., M. J. Rosen, John Wiley & Sons, New York (1989), particularly chapter 3. For example, $Mg^{2+}$ ion at a concentration of 5 mM is useful in the Examples provided below, but higher concentrations may give poorer results.

In practicing certain aspects of the methods, an enzyme substrate is mixed with a sample containing an enzyme that is to be detected or that is being used to screen for, detect or characterize a compound for substrate, inhibitor, activator, or modulator activity. Reaction of the enzyme with the substrate causes an increase (to a more charged species) in the absolute amplitude of the net charge of the substrate, such that the fluorescence of the reacted substrate is greater than the fluorescence of the unreacted substrate. In some embodiments, the substrate has a net charge of zero (neutral net charge), and reaction of the substrate with the enzyme makes the substrate either (1) net negatively charged by (1A) adding or generating a new negatively charged group on the substrate, or (1B) removing or blocking a positively charged group on the substrate; or (2) net positively charged, by (2A) adding or generating a new positively charged group on the substrate, or (2B) removing or blocking a negatively charged group on the substrate. If the substrate has a net charge that is positive or negative, then the enzyme acts on the substrate to change the net charge to be more negative or less negative, provided that the product is more fluorescent than the substrate in the reaction mixture so that enzyme activity can be detected.

For example, reaction (1A) can be accomplished by adding a phosphate group to a hydroxyl group on the substrate (changing a neutrally charged group to a group having a charge of −2, e.g., using a protein kinase), by cleaving a carboxylic ester or amide to produce a carboxyl group (changing a neutrally charged group to a group having a charge of −1, e.g., using an esterase or amidase). Reaction (1B) can be accomplished by reacting an amino or hydrazine group in the substrate with an acetylating enzyme to produce a neutral acetyl ester group, with an N-oxidase enzyme to produce a neutral N-oxide, with an ammonia lyase to remove ammonia, or with an oxidase that causes oxidative deamination, for example. Reaction (2A) can be accomplished, for example, by treating an amide group in the substrate with an amidase to generate a positively charged amino group in the substrate. Reaction (2B) can be accomplished using a decarboxylase enzyme to remove a carboxylic acid or by reacting a carboxyl group with a methyl transferase to form a carboxylic ester, for example. A variety of enzymes capable of performing such transformations are known in the literature (e.g., see C. Walsh, *Enzymatic Reaction Mechanisms*, WH Freeman and Co., New York, (1979), the Worthington Product Catalog (Worthington Enzymes), Sigma Life Sciences Catalog, and the product catalogs of other commercial enzyme suppliers).

In some embodiments, the enzyme substrate has a net negative charge, such as −1, −2, −3, −4, or greater, prior to reaction with the enzyme, but the fluorescence of unreacted substrate is sufficiently low so that increasing the net negative charge of the substrate by reaction with the enzyme causes a detectable increase in fluorescence.

Alternatively, in other embodiments the enzyme substrate may have a net positive charge of +1, +2, +3, +4 or greater, prior to reaction with the enzyme, but fluorescence of unreacted substrate is sufficiently low so that increasing the net positive charge of the substrate by reaction with the enzyme causes a detectable increase in fluorescence.

FIGS. 3A-C illustrate exemplary kinase substrates. FIGS. 3A and 3B illustrate exemplary kinase substrates that can be used to detect a protein kinase that recognizes a peptide consensus sequence for protein kinase p38βII, i.e. $C_{11}$OOLys(Dye 2)ArgArgIleProLeuSerProOOLys($C_{11}$)$NH_2$ (peptide disclosed as SEQ ID NO: 20) (compound 1) and $C_{12}$OOK(dye 2)ArgArgIleProLeuSerProOOK($C_{12}$)$NH_2$ (peptide disclosed as SEQ ID NO: 20) (compound 2). FIG. 3A illustrates an exemplary kinase substrate that can be used to detect a protein kinase that recognizes a peptide consensus sequence for protein kinase Akt3/PKBγ, i.e. $C_{11}$OOK (tet)ArgProArgThrSerSerPheOOK($C_{11}$)$NH_2$ (peptide disclosed as SEQ ID NO: 17) (compound 3). Dye 2 is 5-carboxy-2',7'-dipyridyl-sulfonefluorescein and tet is 2',7', 4,7-tetachloro-5-carboxy fluorescein. Arg, Ile, Pro, Leu, Ser, Thr, Phe and Lys are standard 3-letter codes for arginine, isoleucine, proline, leucine, serine, threonine, phenylalanine and lysine. Exemplary syntheses of compounds 1, 2, and 3 are described in Example 1A.

As can be seen, compound 1 contains a sulfonate anion in the Dye moiety, for a total negative charge of −2. This is offset by the guanidinium groups in the two arginine residues, for a total of two positive charges. Thus, the net charge of the compound is about 0 at pH 7.6.

Compound 1 further includes a protein kinase recognition moiety in the form of a polypeptide containing an amino acid sequence that is recognized by protein kinase p38βII. The recognition moiety also contains an unphosphorylated serine that is capable of being phosphorylated by the kinase. Upon phosphorylation, the net charge of the substrate is changed from neutral to −2, thereby causing an increase in fluorescence.

While the basis for increased fluorescence is not certain, and the inventors do not wish to be bound to a particular theory, it is contemplated that the fluorescent substrates described herein are capable of forming micelles in the reaction mixture due to the hydrophobic moiety, so that the fluorescent moieties quench each other due to their close proximity. Micelle formation can be particularly favored when the substrate is neutrally charged or has a small negative or small positive net charge, so that micelle formation is not prevented by mutual charge repulsion. The putative micelles may be in equilibrium with monomolecular, unassociated species in solution, but the micellar form is the predominant form. The product of the enzyme reaction, however, has an increased net charge (total net negative or total net positive) such that micellar formation by the product is disfavored. The free product fluoresces brightly since it remains relatively free from other fluorescent substrate molecules in the solution.

A comparison of the rates of reaction for a kinase substrate comprising two hydrophobic moieties (i.e. $C_{12}$OOK (dye 2)RRIPLSPOOK($C_{12}$)NH$_2$, (peptide disclosed as SEQ ID NO: 20) used at a concentration of 2 μm and referred to herein as compound 2) versus a kinase substrate comprising a single hydrophobic moiety (i.e.$C_{16}$OOK(dye 2)RRIPLSPNH$_2$, (peptide disclosed as SEQ ID NO: 20) used at a concentration of 4 μm; and referred to herein as compound 4) for several concentrations of ATP (0, 5, 10, 20, 50, 100, 200, and 500 μM) is shown in FIGS. 4A and 4B. R, I, P, L, S, and K are standard 1-letter codes for arginine, isoleucine, proline, leucine, serine and lysine. The rates of the reaction were fitted to the Michaelis-Menton equation. The apparent Km of ATP calculated to be 90 mM for compound 2. The same experiment using compound 4 provided an apparent Km of ATP of >200 mM. Thus, compound 2, with two shorter hydrocarbons, gave a lower Km of ATP than the same sequence with a single hydrocarbon.

In addition to exhibiting lower apparent Km's of ATP, protein kinase substrates with two hydrophobic moieties provide improved signal to noise ratios. As shown in FIG. 5, the kinase substrate $C_{11}$OOK(tet)RPRTSSFOOK$C_{11}$-NH$_2$ (peptide disclosed as SEQ ID NO: 17) (referred to herein as compound 3) comprising two hydrophobic moieties has an improved signal to noise ratio as compared to the kinase substrate comprising one hydrophobic moiety, $C_{15}$OOOK (dye2)RPRTSSF-NH$_2$ (peptide disclosed as SEQ ID NO: 17). R, P, T, S, F are standard 1-letter codes for the amino acids arginine, proline, threonine, seine and phenylalanine. Tet is the fluorescein dye 2',7',4,7-tetachloro-5-carboxy fluorescein.

These results demonstrate that kinase substrates comprising two or more hydrophobic moieties exhibit increased fluorescence over kinase substrates comprising one hydrophobic moiety.

To be effective, not only should a substrate react with the enzyme to form the desired modified product, but also the product should be more fluorescent than the substrate, so that a detectable increase in fluorescence can be observed. Generally, a greater change in fluorescence provides greater assay sensitivity, provided that an adequately low signal-to-noise ratio is achieved. Therefore, it may be desirable to test multiple substrate variants to find a substrate having the most suitable fluorescence properties.

The present disclosure contemplates not only detecting target enzymes, but also methods involving: (1) screening for and/or quantifying enzyme activity in a sample, (2) determining kcat and/or Km of an enzyme or enzyme mixture with respect to selected substrates, (3) detecting, screening for, and/or characterizing substrates of enzymes, (4) detecting, screening for, and/or characterizing inhibitors, activators, and/or modulators of enzyme activity, and (5) determining substrate specificities and/or substrate consensus sequences or substrate consensus structures for selected enzymes.

For example, in screening for enzyme activity, a sample that contains, or may contain, a particular enzyme activity is mixed with a substrate described herein, and the fluorescence is measured to determine whether an increase in fluorescence has occurred. Screening may be performed on numerous samples simultaneously in a multi-well or multi-reaction plate or device to increase the rate of throughput. Kcat and Km may be determined by standard methods, as described, for example, in Fersht, *Enzyme Structure and Mechanism*, 2nd Edition, W.H. Freeman and Co., New York, (1985)).

In some embodiments, the reaction mixture may contain two or more different enzymes. This may be useful, for example, to screen multiple enzymes simultaneously to determine if at least one of the enzymes has a particular enzyme activity.

The substrate specificity of an enzyme can be determined by reacting an enzyme with different substrates having different enzyme recognition moieties, and the activity of the enzyme toward the substrates can be determined based on an increase in their fluorescence. For example, by reacting an enzyme with several different substrates having several different protein kinase recognition moieties, a consensus sequence for preferred substrates of a kinase can be prepared.

Each different substrate may be tested separately in different reaction mixtures, or two or more substrates may be present simultaneously in a reaction mixture. In embodiments in which the different substrates are present simultaneously in the reaction mixture, the substrates can contain the same fluorescent moiety, in which case the observed fluorescent signal is the sum of the signals from enzyme reaction with both substrates. Alternatively, the different substrates can contain different, fluorescently distinguishable fluorescent moieties that allow separate monitoring and/or detection of the reaction of enzyme with each different substrate simultaneously in the same mixture. The fluorescent moieties can be selected such that all or a subset of them are excitable by the same excitation source, or they may be excitable by different excitation sources. They can also be selected to have additional properties, such as, for example, the ability to quench one another when in close proximity thereto, by, for example, collisional quenching, FRET or another mechanism (or combination of mechanisms).

Although not necessary for operation of the methods, the assay mixture may optionally include one or more amphipathic quenching compounds designed to quench the fluorescence of the fluorescent moiety of the substrate (and/or plurality of substrates when more than one substrate is present in the mixture). Such amphipathic quenching molecules generally comprise a hydrophobic moiety capable of integrating the quenching compound into a micelle and a quenching moiety. The hydrophobic moiety can by any moiety capable of integrating the compound into a micelle, and as specific nonlimiting exemplary embodiments, can comprise any of the hydrophobic moieties described previously in connection with, for example, the kinase substrates.

The quenching moiety can include any moiety capable of quenching the fluorescence of the fluorescent moiety of the enzyme substrate used in the assay (or one or more of the substrates if a plurality of substrates are used). Compounds capable of quenching the fluorescence of the various different types of fluorescent dyes discussed above, such as xanthene, fluorescein, rhodamine, cyanine, phthalocyanine and squaraine dyes, are well-known. Such quenching compounds can be non-fluorescent (also referred to as "dark quenchers" or "black hole quenchers") or, alternatively, they may themselves be fluorescent. Examples of suitable non-fluorescent dark quenchers that can comprise the quenching moiety include, but are not limited to, Dabcyl, Dabsyl, the various non-fluorescent quenchers described in U.S. Pat. No. 6,080,868 (Lee et al.) and the various non-fluorescent quenchers described in WO 03/019145 (Ewing et al.). Examples of suitable fluorescent quenchers include, but are not limited to, the various fluorescent dyes described above in connection with kinase substrates.

The ability of a quencher to quench the fluorescence of a particular fluorescent moiety may depend upon a variety of different factors, such as the mechanisms of action by which the quenching occurs. The mechanism of the quenching is not critical to success, and may occur, for example, by collision, by FRET, by another mechanisms or combination of mechanisms. The selection of a quencher for a particular application can be readily determined empirically. As a specific example, the dark quencher Dabcyl and the fluorescent quencher TAMRA have been shown to effectively quench the fluorescence of a variety of different fluorophores. In a specific embodiment, a quencher can be selected based upon its spectral overlap properties spectral overlap with the fluorescent moiety. For example, a quencher can be selected that has an absorbance spectrum that sufficiently overlaps the emission spectrum of the fluorescent moiety such that the quencher quenches the fluorescence of the fluorescent moiety are in close proximity to one another, such as when the quencher molecule and substrate including the quencher moiety are integrated into the same micelle.

In embodiments in which a plurality of substrates are present in the assay, such as the multiplexed embodiments described above, it may be desirable to select a quenching moiety that can quench the fluorescence of the fluorescent moieties of all of the substrates present in the assay.

The hydrophobic and quenching moieties can be connected in any way that permits them to perform their respective functions. In some embodiments, only one of the two hydrophobic moieties may be linked either directly or via a linker to a quenching moiety. In other embodiment, both hydrophobic moieties may be linked either directly or via a linker to a quenching moiety. As a specific example, one hydrophobic moiety may be linked directly to the quenching moiety without the aid of a linker. Non-limiting examples of such quenching compounds include molecules in which a dye (e.g. a rhodamine or fluorescein dye) which contains a primary amino group (or other suitable group) is acylated with a fatty acid. As another specific example, the linkage may be mediated by way of a linker. The identity of the linker is not critical, and can include a peptide segment (or analog thereof). Although in many embodiments the peptide segment will not include an enzyme recognition moiety recognized by the enzyme(s) being assayed, it may optionally include such a moiety(ies). As a specific example, the quencher molecule can be a derivative or analog of any of the kinase or other enzyme substrates described herein in which the fluorescent moiety is replaced with a quenching moiety and the sequence of the enzyme recognition moiety is modified such that it is not recognized by the enzyme(s) being assayed in the sample.

Like the enzyme substrate, the quencher molecule can be designed to have specified charge characteristics.

Detecting, screening for, and/or characterizing inhibitors, activators, and/or modulators of enzyme activity can be performed by forming reaction mixtures containing such known or potential inhibitors, activators, and/or modulators and determining the extent of increase or decrease (if any) in fluorescence signal relative to the signal that is observed without the inhibitor, activator, or modulator. Different amounts of these substances can be tested to determine parameters such as Ki (inhibition constant), $K_H$ (Hill coefficient), Kd (dissociation constant) and the like to characterize the concentration dependence of the effect that such substances have on enzyme activity.

Detection of fluorescent signal can be performed in any appropriate way. Advantageously, substrates of the various embodiments can be used in a continuous monitoring phase, in real time, to allow the user to rapidly determine whether enzyme activity is present in the sample, and optionally, the amount or specific activity of the enzyme. The fluorescent signal is measured from at least two different time points, usually until an initial velocity (rate) can be determined. The signal can be monitored continuously or at several selected time points. Alternatively, the fluorescent signal can be measured in an end-point embodiment in which a signal is measured after a certain amount of time, and the signal is compared against a control signal (before start of the reaction), threshold signal, or standard curve.

IV. Kits

Also provided are kits for performing the methods described herein. In some embodiments, the kit comprises at least one enzyme substrate for detecting a target enzyme, and a buffer for preparing a reaction mixture that facilitates the enzyme reaction. The buffer may be provided in a container in dry form or liquid form. The choice of a particular buffer may depend on various factors, such as the pH optimum for the enzyme to be detected, the solubility and fluorescence properties of the fluorescent moiety in the substrate, and the pH of the sample from which the target enzyme is obtained. The buffer is usually added to the reaction mixture in an amount sufficient to produce a particular pH in the mixture. In some embodiments, the buffer is provided as a stock solution having a pre-selected pH and buffer concentration. Upon mixture with the sample, the buffer produces a final pH that is suitable for the enzyme assay, as discussed above. The pH of the reaction mixture may also be titrated with acid or base to reach a final, desired pH. The kit may additionally include other components that are beneficial to enzyme activity, such as salts (e.g., KCl, NaCl, or NaOAc), metal salts (e.g., Ca2+ salts such as $CaCl_2$, $MgCl_2$, $MnCl_2$, $ZnCl_2$, or Zn(OAc), detergents (e.g., TWEEN 20), and/or other components that may be useful for a particular enzyme. These other components can be provided separately from each other or mixed together in dry or liquid form.

The enzyme substrate can also be provided in dry or liquid form, together with or separate from the buffer. To facilitate dissolution in the reaction mixture, the enzyme substrate can be provided in an aqueous solution, partially aqueous solution, or non-aqueous stock solution that is miscible with the other components of the reaction mixture. For example, in addition to water, a substrate solution may also contain a cosolvent such as dimethyl formamide, dimethylsulfonate, methanol or ethanol, typically in a range of 1%-10% (v:v).

For detection of protein kinase activity, the kit may also contain a phosphate-donating group, such as ATP, GTP, ITP (inosine triphosphate) or other nucleotide triphosphate or nucleotide triphosphate analog that can be used by the kinase to phosphorylate the substrate.

The operation of the various compositions and methods can be further understood in light of the following non-limiting examples, which should not be construed as limiting the scope of the present teachings in any way.

EXAMPLES

Example 1

Preparation of Protein Kinase Substrates

Resins and reagents for peptide synthesis, Fmoc amino acids, 5-carboxyfluorescein succinimidyl ester were obtained from Applied Biosystems (Foster City, Calif.). Fmoc-Lys(Mtt)—OH, Fmoc-Ser(OPO(OBzl(OH)—OH and Fmoc-Dpr(ivDde) were obtained from Novabiochem. All other chemicals and buffers were obtained from Sigma/Aldrich.

Peptide synthesis was performed on an Applied Biosystems Model 433A Peptide Synthesizer. HPLC was performed on an Agilent 1100 series HPLC. UV-Vis measurements were performed on a Cary 3E UV-Vis spectrophotometer. MALDI Mass spectral data were obtained on an Applied Biosystems Voyager using cyano-4-hydroxycinnamic acid as matrix material.

An exemplary enzyme substrate useful for detecting protein kinase p38βII, $C_{12}$-OOK(dye2)RRIPLSPOOK($C_{12}$)-amide (peptide disclosed as SEQ ID NO: 20) (compound 1), was prepared as follows. The peptide OOK(ivDde)RRIPLSPOOK(Mtt) (peptide disclosed as SEQ ID NO: 20) was constructed via solid phase peptide synthesis using standard FastMoc™ chemistry on 125 mg of Fmoc-PAL-PEG-PS resin at 0.16 mmol/g, a solid support which results in a carboxamide peptide. A portion of the final protected peptide-resin (20 mg, 2 μmol peptide) was transferred to a 1.5 ml Eppendorf tube and treated with 1 mL of 5% trifluoroacetic acid (TFA) in dichloromethane (DCM), giving a characteristic yellow trityl color. The resin was treated with additional 1 mL portions of 5% TFA until the washes were colorless. The resin was washed with DCM (1 mL). Dodecanoic acid (20 mg), HBTU/HOBT solution (0.1 mL) and diisopropylethylamine (0.04 mL) were added to the resin and the mixture was agitated gently for 20 min. The resin was washed with DMF (5×1 mL) and treated with 10% hydrazine in DMF for ten minutes. 5-Carboxy-2',7'-dipyridylsulfonefluorescein (10 mg), HBTU/HOBT solution (0.1 mL) and diisopropylethylamine (0.04 mL) were added to the resin and the mixture agitated for 45 minutes. The resin was washed with 8×1 mL DMF, 1×1 mL acetonitrile. The peptide was cleaved from the resin with 1 mL cleavage solution (950 μL TFA, 50 μL water). After 1.5 to 2 h the mixture was filtered and the filtrate concentrated to dryness on a rotary evaporator. The residue was dissolved in water (0.5 mL) and a portion purified by reverse-phase HPLC (Metachem Technologies column: 150×4.6 mm, Polaris C18, 5 μm) using a 30% to 70% gradient over 10 min of 0.1% TFA in acetonitrile vs. 0.1% TFA in water. The dye-labeled peptide was analyzed by MALDI mass spectrometry, which resulted in the expected M/z=2281. The peptide solution was evaporated to dryness, redissolved in water, and quantitated as described in Example 2. The extinction coefficient of 5-Carboxy-2',7'-dipyridylsulfonefluorescein was assumed to be 80,000 $cm^{-1}M^{-1}$.B.

Example 2

Detection of Protein Kinase Activity

Kinase assays were performed using Corning 384-well, black, non-binding surface (NBS), microwell plates. Fluorescence was read in real time using a Molecular Dynamics Gemini XS plate reader, with excitation and emission set at 500 and 550 respectively. The plate was read every minute for one hour at ambient temperature Concentrations of dye-labeled peptides were determined by dilution of the purified peptides into dimethylformamide (200 μL) with 1 M NaOH (5 μL) and measuring the absorbance of either 5-carboxy-2',7'-dipyridyl-sulfonefluorescein (i.e. dye2) at its absorbance maximum (548 nm) or 2',7',4,7-tetachloro-5-carboxy fluorescein (i.e. 2',7'-dichloro-5-carboxy-4,7-dichlorofluorescein or "tet") at its absorbance maximum (541 nm). The extinction coefficient of both dyes was assumed to be 80,000 $cm^{-1}M^{-1}$.

A reaction solution was prepared containing compound 1 (2 mM) 20 mM Tris buffer, pH 7.4, MgC12 (5 mM), DTT (5 mM) and p38bII (14 nM). The solution was pipetted into wells of a 384-well plate (10 mL per well). Varying concentrations of ATP (final conc 0, 5, 10, 20, 50, 100, 200, 500 mM) were added to the wells to initiate the kinase reaction. The plate was read at 500 nm excitation, 550 nm emission, each minute for 1 hour. The results are shown in FIG. 4. The rates of the reaction were fitted to the Michaelis-Menton equation and the apparent Km of ATP calculated to be 90 μM for $C_{12}$OOK(dye2)RRIPLSPOOK($C_{12}$)$NH_2$ (peptide disclosed as SEQ ID NO: 20) (compound 2). The same experiment using $C_{16}$OOOK(dye2)RRIPLSP$NH_2$ (peptide disclosed as SEQ ID NO: 20) (compound 4) provided an apparent Km of ATP of >200 μM. Thus, compound 2, with two shorter hydrocarbons, gave a lower Km of ATP than the same sequence with a single hydrocarbon.

All literature and similar materials cited in this application, including but not limited to, patents, patent applications, articles, books, treatises, regardless of the format of such literature and similar materials, are expressly incorporated by reference in their entirety for any purpose.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

---

What is claimed is:

1. A substrate compound comprising two or more hydrophobic moieties capable of integrating the compound into a micelle, one or more non-proteinaceous fluorescent moiety(ies), and an enzyme recognition moiety, wherein one of said two or more hydrophobic moieties is located N-terminal to said enzyme recognition moiety and another of said two or more hydrophobic moieties is located C-terminal to said enzyme recognition moiety.

2. The substrate compound of claim 1 which has a net neutral charge in aqueous solution at a pH of about pH 7.6.

3. The substrate compound of claim 1 in which the enzyme recognition moiety comprises a protein kinase recognition sequence including at least one unphosphorylated residue capable of being phosphorylated by a protein kinase.

4. The substrate compound of claim 3 in which the at least one unphosphorylated residue is tyrosine, serine or threonine.

5. The substrate compound of claim 3 in which the protein kinase recognition sequence is recognized by a TK kinase, an AGC kinase, a CAMK kinase, a CMGC kinase, an STE kinase, a TKL kinase, a CKI kinase or a kinase belonging to the group "other."

6. The substrate compound of claim 3 in which the protein kinase recognition sequence is recognized by a protein kinase A, a protein kinase C, a Src kinase, a Lyn kinase, a Fyn kinase, an Akt kinase, a MAP kinase, a MAPKAP2 kinase, cAMP dependent kinase, a PKB kinase, or a p38βII kinase.

7. The substrate compound of claim 3 in which the protein kinase recognition sequence comprises a peptide sequence selected from the group consisting of:

| | |
|---|---|
| -R-R-X-S/T-Z-; | (SEQ ID NO:1) |
| -R-X-X-S/T-F-F-; | (SEQ ID NO:2) |
| -S/T-P-X-R/K-; | (SEQ ID NO:3) |
| -P-X-S/T-P-; | (SEQ ID NO:4) |
| -K-K-K-K-R-F-S-F-K-; | (SEQ ID NO:5) |
| -X-R-X-X-S-X-R-X-; | (SEQ ID NO:6) |
| -L-R-R-L-S-D-S-N-F-; | (SEQ ID NO:7) |
| -K-K-L-N-R-T-L-T-V-A-; | (SEQ ID NO:8) |
| -E-E-I-Y-E/G-X-F-; | (SEQ ID NO:9) |
| -E-I-Y-E-X-I/V-; | (SEQ ID NO:10) |
| -I-Y-M-F-F-F-; | (SEQ ID NO:11) |
| -Y-M-M-M-; | (SEQ ID NO:12) |
| -E-E-E-Y-F-; | (SEQ ID NO:13) |
| -L-R-R-A-S-L-G-; | (SEQ ID NO:14) |
| -R-Q-G-S-F-R-A-; | (SEQ ID NO:15) |
| -R-I-G-E-G-T-Y-G-V-V-R-R-; | (SEQ ID NO:16) |
| -R-P-R-T-S-S-F-; | (SEQ ID NO:17) |
| -P-R-T-P-G-G-R-; | (SEQ ID NO:18) |
| -R-L-N-R-T-L-S-V-; | (SEQ ID NO:19) |
| -R-R-I-P-L-S-P-; | (SEQ ID NO:20) | and analogs and conservative mutants thereof, wherein X represents any residue and Z represents a hydrophobic residue.

8. The substrate compound of claim 3 which has a net neutral charge in aqueous solution at a pH of about pH 7.6.

9. The substrate compound of claim 3 which has the structure:

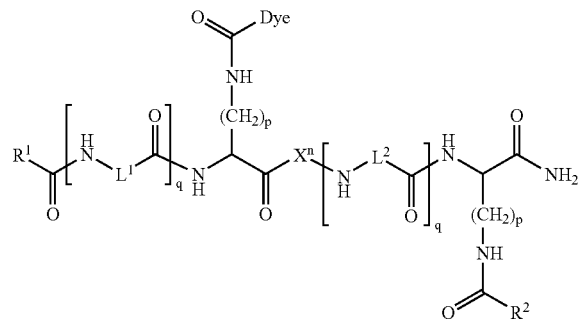

wherein:
each q is, independently of the other, 0 or 1;
each p is, independently of the other, an integer ranging from 1 to 6;
$R^1$ is a substituted or unsubstituted, saturated or unsaturated, linear or branched alkyl containing from 6 to 30 carbon atoms;
$R^2$ is a substituted or unsubstituted, saturated or unsaturated, linear or branched alkyl containing from 6 to 30 carbon atoms;
$L^1$ represents a linker;
$X^n$ comprises the protein kinase recognition sequence;
$L^2$ represents a linker; and
Dye represents a fluorescent dye.

10. The substrate compound of claim 9 in which both q's are 1 and $L^1$ and $L^2$ are each $-[(CH_2CH_2O)_n-CH_2]_m-$, where each n is, independently of the other, an integer ranging from 1 to 6 and each m is, independently of the other, an integer ranging from 1 to 6.

11. The substrate compound of claim 10 in which each n is 2 and each m is, independently of the other, selected from 2, 3 and 4.

12. The substrate compound of claim 9 in which Dye comprises a fluorescein or a rhodamine dye.

13. The substrate compound of claim 9 in which $X^n$ is a peptide selected from the group consisting of:

```
-R-R-X-S/T-Z-              (SEQ ID NO:1);
-R-X-X-S/T-F-F-            (SEQ ID NO:2);
-S/T-P-X-R/K-              (SEQ ID NO:3);
-P-X-S/T-P-                (SEQ ID NO:4);
-K-K-K-K-R-F-S-F-K-        (SEQ ID NO:5);
-X-R-X-X-S-X-R-X-          (SEQ ID NO:6);
-L-R-R-L-S-D-S-N-F-        (SEQ ID NO:7);
-K-K-L-N-R-T-L-T-V-A-      (SEQ ID NO:8);
-E-E-I-Y-E/G-X-F-          (SEQ ID NO:9);
-E-I-Y-E-X-I/V-            (SEQ ID NO:10);
-I-Y-M-F-F-F-              (SEQ ID NO:11);
-Y-M-M-M-                  (SEQ ID NO:12);
-E-E-E-Y-F-                (SEQ ID NO:13);
-L-R-R-A-S-L-G-            (SEQ ID NO:14);
-R-Q-G-S-F-R-A-            (SEQ ID NO:15);
-R-I-G-E-G-T-Y-G-V-V-R-R-  (SEQ ID NO:16);
-R-P-R-T-S-S-F-            (SEQ ID NO:17);
-P-R-T-P-G-G-R-            (SEQ ID NO:18);
-R-L-N-R-T-L-S-V-          (SEQ ID NO:19); and
-R-R-I-P-L-S-P-            (SEQ ID NO:20).
```

14. The substrate compound of claim 3 in which each hydrophobic moiety comprises a substituted or unsubstituted, saturated or unsaturated hydrocarbon containing from 6 to 30 carbon atoms.

15. The substrate compound of claim 14 in which the hydrocarbon is a linear, branched or cyclic, saturated or unsaturated alkyl.

16. The substrate compound of claim 3 in which the one or more non-proteinaceous fluorescent moiety(ies) comprises a dye selected from a xanthene dye, a rhodamine dye, a fluorescein dye, a cyanine dye, a phthalocyanine dye, a squaraine dye and a bodipy dye.

17. The substrate compound of claim 3 in which the one or more non-proteinaceous fluorescent moiety(ies) comprises a fluorescence donor moiety and a fluorescence acceptor moiety.

18. The substrate compound of claim 17 in which the fluorescence donor moiety comprises a fluorescein dye.

19. The substrate compound of claim 17 in which the fluorescence acceptor moiety comprises a fluorescein or a rhodamine dye.

20. The substrate compound of claim 19 in which the fluorescence donor moiety comprises a fluorescein dye.

21. The substrate compound of claim 3 in which the one or more non-proteinaceous fluorescent moiety(ies) comprises fewer than 150 atoms.

22. The substrate compound of claim 3 in which one hydrophobic moiety is linked to the enzyme recognition moiety through the one or more non-proteinaceous fluorescent moiety(ies), optionally via a linker, and another hydrophobic moiety is linked to the enzyme recognition moiety through one or more optional linkers.

23. The substrate compound of claim 3 in which two of the two or more hydrophobic moieties are linked to one another through the one or more non-proteinaceous fluorescent moiety(ies).

24. The substrate compound of claim 3 in which one of the two or more hydrophobic moieties, the one or more non-proteinaceous fluorescent moiety(ies) and the enzyme recognition moiety are linked to each other via a trivalent linker.

25. The substrate compound of claim 3 in which one of the two or more hydrophobic moieties is linked to the one or more non-proteinaceous fluorescent moiety(ies) by a linker that does not include a part of the enzyme recognition moiety.

26. The substrate compound of claim 3 in which at least one of the two or more hydrophobic moieties is linked to the one or more non-proteinaceous fluorescent moiety(ies) by a linker that includes at least a part of the enzyme recognition moiety.

27. The substrate compound of claim 1 in which the enzyme recognition moiety comprises a phosphatase recognition sequence including at least one phosphorylated residue capable of being dephosphorylated by a phosphatase.

28. The substrate compound of claim 27 which has a net neutral charge in aqueous solution at a pH of about pH 7.6.

29. A method of detecting phosphorylation activity of one or more protein kinases in a sample, comprising the steps of:
contacting the sample with a composition comprising a protein kinase substrate which comprises (1) a protein kinase recognition sequence according to claim 3 containing at least one unphosphorylated residue capable of being phosphorylated by a protein kinase, (2) two or more hydrophobic moieties capable of integrating the substrate into a micelle, and (3) one or more non-proteinaceous fluorescent moiety(ies), under conditions effective to allow phosphorylation of said residue when the protein kinase is present in the sample, thereby increasing a fluorescence signal produced by the one or more non-proteinaceous fluorescent moiety(ies); and
detecting a fluorescence signal, where an increase in the fluorescence signal indicates the presence and/or quantity of protein kinase phosphorylation activity in the sample.

30. A method of identifying a compound that modulates phosphorylation activity of a protein kinase, comprising the steps of:
contacting the protein kinase with a composition comprising a protein kinase substrate which comprises (1) a protein kinase recognition sequence according to claim 3 containing at least one unphosphorylated residue capable of being phosphorylated by a protein kinase, (2) two or more hydrophobic moieties capable of integrating the substrate into a micelle, and (3) one or more non-proteinaceous fluorescent moiety(ies), in the presence of a candidate compound and under conditions effective to allow phosphorylation of said residue by the protein kinase, thereby increasing a fluorescence signal produced by the one or more non-proteinaceous fluorescent moiety(ies); and
detecting a fluorescence signal, where a change in the fluorescence signal as compared to a control reaction or a standard curve indicates that the candidate compound modulates the activity of the protein kinase.

31. A substrate compound comprising two or more hydrophobic moieties capable of integrating the compound into a micelle, one or more fluorescent moiety(ies), and an enzyme recognition moiety, wherein one of said two or more hydrophobic moieties is located N-terminal to said enzyme recognition moiety and another of said two or more hydrophobic moieties is located C-terminal to said enzyme recognition moiety, and wherein said substrate compound has a molecular weight of less than 5000 daltons.

* * * * *

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

```
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (4)
<223> OTHER INFORMATION: Ser or Thr
<220> FEATURE:
<221> NAME/KEY: MOD_RES
<222> LOCATION: (5)
<223> OTHER INFORMATION: Hydrophobic amino acid

<400> SEQUENCE: 1

Arg Arg Xaa Xaa Xaa
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (4)
<223> OTHER INFORMATION: Ser or Thr

<400> SEQUENCE: 2

Arg Xaa Xaa Xaa Phe Phe
 1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ser or Thr
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (4)
<223> OTHER INFORMATION: Arg or Lys

<400> SEQUENCE: 3

Xaa Pro Xaa Xaa
 1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
```

```
<221> NAME/KEY: MOD_RES
<222> LOCATION: (3)
<223> OTHER INFORMATION: Ser or Thr

<400> SEQUENCE: 4

Pro Xaa Xaa Pro
  1

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Lys Lys Lys Arg Phe Ser Phe Lys
  1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)
<223> OTHER INFORMATION: Variable amino acid

<400> SEQUENCE: 6

Xaa Arg Xaa Xaa Ser Xaa Arg Xaa
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Arg Arg Leu Ser Asp Ser Asn Phe
  1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Lys Leu Asn Arg Thr Leu Thr Val Ala
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Glu or Gly
<220> FEATURE:
<221> NAME/KEY: MOD_RES
<222> LOCATION: (6)
<223> OTHER INFORMATION: Variable amino acid

<400> SEQUENCE: 9

Glu Glu Ile Tyr Xaa Xaa Phe
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (6)
<223> OTHER INFORMATION: Ile or Val

<400> SEQUENCE: 10

Glu Ile Tyr Glu Xaa Xaa
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Tyr Met Phe Phe Phe
  1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Met Met Met
  1

<210> SEQ ID NO 13
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 13

Glu Glu Glu Tyr Phe
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Arg Arg Ala Ser Leu Gly
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gln Gly Ser Phe Arg Ala
  1               5

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ile Gly Glu Gly Thr Tyr Gly Val Val Arg Arg
  1               5                  10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Pro Arg Thr Ser Ser Phe
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Arg Thr Pro Gly Gly Arg
  1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Leu Asn Arg Thr Leu Ser Val
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Ile Pro Leu Ser Pro
 1               5
```